US012797004B2

(12) United States Patent
Kawamura

(10) Patent No.: US 12,797,004 B2

(45) Date of Patent: Nov. 17, 2026

(54) IMAGE PROCESSING DEVICE, IMAGE PROCESSING METHOD, IMAGE PROCESSING PROGRAM, LEARNING DEVICE, LEARNING METHOD, AND LEARNING PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/184,353

(22) Filed: Apr. 21, 2025

(65) Prior Publication Data

US 2025/0248646 A1 Aug. 7, 2025

Related U.S. Application Data

(63) Continuation of application No. PCT/JP2023/032691, filed on Sep. 7, 2023.

(30) Foreign Application Priority Data

Oct. 27, 2022 (JP) ................................ 2022-172746

(51) Int. Cl.
*A61B 5/00* (2006.01)
*A61B 6/00* (2024.01)
(Continued)

(52) U.S. Cl.
CPC ............ *A61B 5/4509* (2013.01); *A61B 6/482* (2013.01); *A61B 6/505* (2013.01); *A61B 6/5282* (2013.01);
(Continued)

(58) Field of Classification Search
CPC ....... A61B 5/4509; A61B 6/482; A61B 6/505; A61B 6/5282; A61B 6/5217; A61B 6/00;
(Continued)

(56) References Cited

U.S. PATENT DOCUMENTS

2016/0140720 A1 5/2016 Naito
2017/0354385 A1 12/2017 Lerch
(Continued)

FOREIGN PATENT DOCUMENTS

JP 2015-043959 A 3/2015
JP 2019-115558 A 7/2019
(Continued)

OTHER PUBLICATIONS

The KR-20220134375-A machine translation (Year: 2022).*
(Continued)

*Primary Examiner* — Alexei Bykhovski

(74) *Attorney, Agent, or Firm* — Studebaker Brackett PLLC

(57) ABSTRACT

A processor acquires a structure image representing at least one structure in a subject based on at least one radiation image of the subject, and derives a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

14 Claims, 20 Drawing Sheets

(51) Int. Cl.
*A61B 6/50* (2024.01)
*G06T 5/50* (2006.01)

(52) U.S. Cl.
CPC ...... *G06T 5/50* (2013.01); *G06T 2207/20081* (2013.01); *G06T 2207/20084* (2013.01); *G06T 2207/20224* (2013.01)

(58) Field of Classification Search
CPC ............. G06T 5/50; G06T 2207/20081; G06T 2207/20084; G06T 2207/20224; G06T 7/0012; G06T 2207/10081; G06T 2207/10116; G06T 2207/30008
See application file for complete search history.

(56) References Cited

U.S. PATENT DOCUMENTS

| | | | |
|---|---|---|---|
| 2018/0122094 A1 | 5/2018 | Naito | |
| 2019/0362492 A1* | 11/2019 | Kawamura | G06T 7/0016 |
| 2020/0082526 A1 | 3/2020 | Murphy et al. | |
| 2020/0311975 A1 | 10/2020 | Matsuura | |
| 2021/0369224 A1 | 12/2021 | Okano et al. | |
| 2022/0051398 A1 | 2/2022 | Watanabe et al. | |
| 2022/0265228 A1 | 8/2022 | Shimizu et al. | |
| 2022/0287665 A1 | 9/2022 | Taki | |
| 2022/0313192 A1 | 10/2022 | Kawamura | |
| 2022/0323032 A1 | 10/2022 | Kawamura | |
| 2022/0335605 A1 | 10/2022 | Taki | |
| 2024/0202973 A1* | 6/2024 | Reimer | G06T 7/344 |

FOREIGN PATENT DOCUMENTS

| | | | |
|---|---|---|---|
| JP | 2022-106894 A | 7/2022 | |
| JP | 2022-140050 A | 9/2022 | |
| JP | 2022-158574 A | 10/2022 | |
| KR | 10-2022-0134375 A | 10/2022 | |
| KR | 20220134375 A * | 10/2022 | G06T 7/60 |
| WO | 2020/166561 A1 | 8/2020 | |
| WO | 2021/100513 A1 | 5/2021 | |

OTHER PUBLICATIONS

The extended European search report issued by the European Patent Office on Sep. 19, 2025, which corresponds to European Patent Application No. 23882263.9-1122 and is related to U.S. Appl. No. 19/184,353.

International Search Report issued in PCT/JP2023/032691; mailed Oct. 10, 2023.

International Preliminary Report on Patentability (Chapter I) and Written Opinion of the International Searching Authority issued in PCT/JP2023/032691; issued Apr. 29, 2025.

* cited by examiner

IMAGE PROCESSING DEVICE, IMAGE PROCESSING METHOD, IMAGE PROCESSING PROGRAM, LEARNING DEVICE, LEARNING METHOD, AND LEARNING PROGRAM

CROSS-REFERENCE TO RELATED APPLICATIONS

This application is a continuation of International Application No. PCT/JP2023/032691, filed on Sep. 7, 2023, which claims priority from Japanese Patent Application No. 2022-172746, filed on Oct. 27, 2022. The entire disclosure of each of the above applications is incorporated herein by reference.

BACKGROUND

Technical Field

The present invention relates to an image processing device, an image processing method, an image processing program, a learning device, a learning method, and a learning program.

Related Art

In the related art, energy subtraction processing using two radiation images obtained by irradiating a subject with two types of radiation having different energy distributions by using the fact that an attenuation amount of the transmitted radiation differs depending on the substance constituting the subject has been known. In addition, various methods for deriving composition information of the human body, such as a bone density, a thickness of a soft part, a thickness of fat, and a thickness of muscle, by the energy subtraction processing have also been proposed (for example, see WO2020/166561A).

In order to effectively perform the diagnosis of the subject using such composition information, a relationship between the positioning of the subject with respect to the transmission path of the radiation at the time of imaging is important. For example, in a case in which the radiation is emitted from the front of the subject, in a case in which the position of the subject changes due to the rotation of the subject, the incidence angle of the radiation with respect to the subject deviates from the reference incidence angle, and as a result, the thickness of the subject on the transmission path of the radiation changes. In a case in which the thickness of the subject changes in this way, it is not possible to accurately compare the composition information between the radiation images captured at different positions. In addition, in a case where the positioning of the subject is to be performed accurately at the time of imaging, it takes time to perform the imaging.

SUMMARY OF THE INVENTION

The present disclosure has been made in view of the above circumstances, and an object of the present disclosure is to enable accurate derivation of a composition regardless of positioning of a subject.

An image processing device according to the present disclosure comprising at least one processor, in which the processor acquires a structure image representing at least one structure in a subject based on at least one radiation image of the subject, and derives a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

In the image processing device according to the present disclosure, the processor may acquire a first radiation image and a second radiation image acquired by imaging a subject including a bone part and a soft part with radiation having different energy distributions, and derive the structure image by performing weighting subtraction on the first radiation image and the second radiation image.

In addition, in the image processing device according to the present disclosure, the processor may remove scattered ray components of the first radiation image and the second radiation image to derive a first primary ray image and a second primary ray image, and derive the structure image based on the first primary ray image and the second primary ray image.

In addition, in the image processing device according to the present disclosure, the structure may be a bone part included in the subject, and the composition information may be a bone density.

In this case, the bone part may be a femur or a vertebra, particularly a lumbar vertebra.

In the image processing device according to the present disclosure, the structure may be a soft part included in the subject, and the composition information may be a thickness of the soft part.

According to the present disclosure, a learning device comprising:

at least one processor, in which the processor performs training of a neural network using training data including a training structure image including at least one structure in a subject, a deviation angle of radiation with respect to a reference position for the structure included in the training structure image, and composition information of the structure included in the training structure image at the reference position, and constructs a trained model that outputs an estimation result of the deviation angle of the radiation with respect to the reference position of the structure and the composition information of the structure at the reference position included in the structure image by input of the structure image including at least one structure in the subject, by the training.

In the learning device according to the present disclosure, the processor may derive the training structure image by projecting the structure included in a three-dimensional image of the subject based on a deviation angle with respect to the reference position, and derive the training data by deriving composition information of the structure as composition information of the structure at the reference position in a case where the structure included in the three-dimensional image is projected in a reference direction in which the structure is the reference position.

In addition, in the learning device according to the present disclosure, the structure may be a bone part, and the processor may derive a three-dimensional bone density of the bone part included in the three-dimensional image, and derive a two-dimensional bone density of the bone part as the composition information of the structure at the reference position by multiplying the three-dimensional bone density by a thickness of the bone part in the reference direction.

An image processing method according to the present disclosure comprising:

acquiring a structure image representing at least one structure in a subject based on at least one radiation image of the subject; and deriving a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

According to the present disclosure, a learning method comprising:

performing training of a neural network using training data including a training structure image including at least one structure in a subject, a deviation angle of radiation with respect to a reference position for the structure included in the training structure image, and composition information of the structure included in the training structure image at the reference position, and constructing a trained model that outputs an estimation result of the deviation angle of the radiation with respect to the reference position of the structure and the composition information of the structure at the reference position included in the structure image by input of the structure image including at least one structure in the subject, by the training.

According to the present disclosure, an image processing program causing a computer to execute a process comprising:

acquiring a structure image representing at least one structure in a subject based on at least one radiation image of the subject; and deriving a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

According to the present disclosure, a learning program causing a computer to execute a process comprising:

performing training of a neural network using training data including a training structure image including at least one structure in a subject, a deviation angle of radiation with respect to a reference position for the structure included in the training structure image, and composition information of the structure included in the training structure image at the reference position, and constructing a trained model that outputs an estimation result of the deviation angle of the radiation with respect to the reference position of the structure and the composition information of the structure at the reference position included in the structure image by input of the structure image including at least one structure in the subject, by the training.

According to the present disclosure, the composition can be accurately derived regardless of the positioning of the subject.

DETAILED DESCRIPTION

Figure 1:
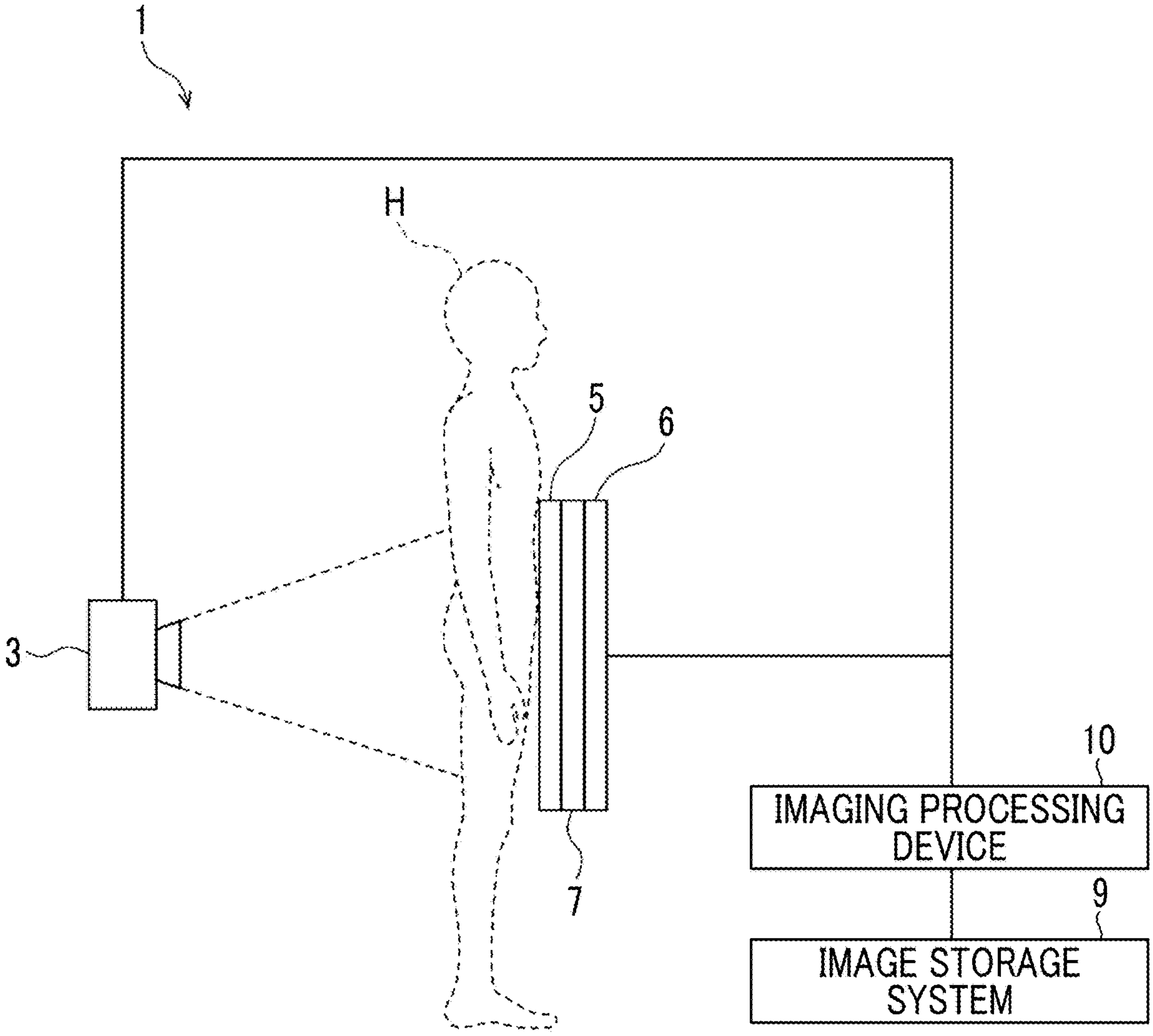
FIG. 1 is a block diagram schematically showing a configuration of a radiography system to which an image processing device and a learning device according to an embodiment of the present disclosure are applied.

Hereinafter, embodiments of the present disclosure will be described with reference to drawings. FIG. 1 is a schematic block diagram showing a configuration of a radiography system to which an image processing device and a learning device according to an embodiment of the present disclosure are applied. As shown in FIG. 1, a radiography system according to the present embodiment comprises an imaging apparatus 1 and an image processing device and a learning device (hereinafter, may be represented by the image processing device) 10 according to the present embodiment.

The imaging apparatus 1 is an imaging apparatus for performing energy subtraction by a so-called one-shot method for converting radiation, such as X-rays, emitted from a radiation source 3 and transmitted through a subject H into energy and irradiating a first radiation detector 5 and a second radiation detector 6 with the converted radiation. During the imaging, as shown in FIG. 1, the first radiation detector 5, a radiation energy conversion filter 7 made of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation also including so-called soft rays is acquired. Further, in the second radiation detector 6, a second radiation image G2 of the subject H by high-energy radiation from which the soft ray is removed is acquired. Note that both the first and second radiation images G1 and G2 are two-dimensional images that are transmission images of the subject acquired by simple imaging in which the radiation is emitted to the subject H once. Thus, both the first and second radiation images G1 and G2 are simple radiation images. The first and second radiation images are input to the image processing device 10.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

The image processing device 10 is connected to the image storage system 9 via a network (not shown).

The image storage system 9 is a system that stores image data of the radiation image captured by the imaging apparatus 1. The image storage system 9 extracts an image corresponding to a request from the image processing device 10 from the stored radiation image and transmits the extracted image to a request source device. Specific examples of the image storage system 9 include picture archiving and communication systems (PACS). In the present embodiment, the image storage system 9 stores a three-dimensional image V0 of the subject for deriving the training data as described below. The three-dimensional image V0 can be acquired by a computed tomography (CT) apparatus, a magnetic resonance imaging (MRI) apparatus, or the like. In the present embodiment, it is assumed that a CT image is stored as the three-dimensional image V0. The image storage system 9 may store the training data derived as described below.

Figure 2:
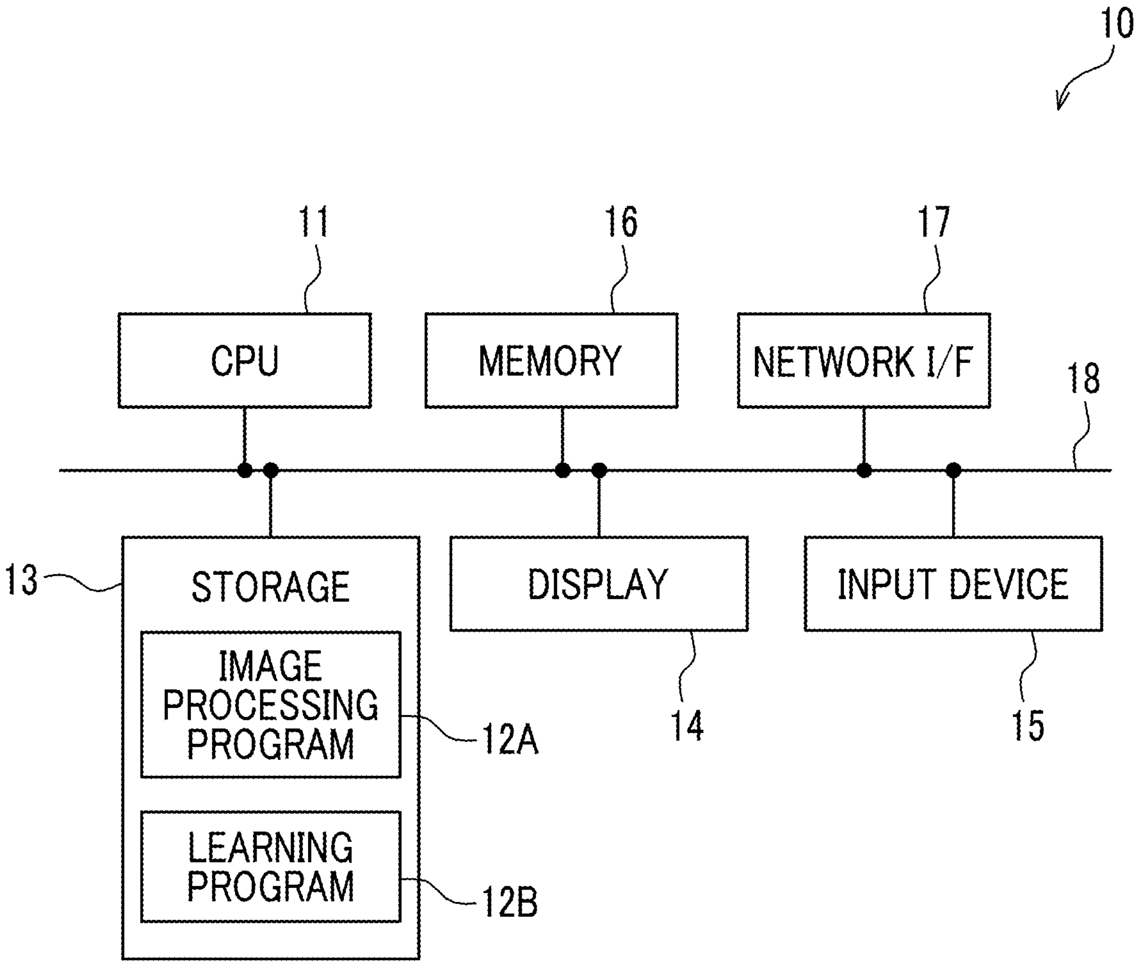
FIG. 2 is a diagram showing a schematic configuration of an image processing device and a learning device according to the embodiment of the present disclosure.

Then, the image processing device according to the present embodiment will be described. First, a hardware configuration of the image processing device according to the present embodiment will be described with reference to FIG. 2. As shown in FIG. 2, the image processing device 10 is a computer, such as a workstation, a server computer, and a personal computer, and comprises a central processing unit (CPU) 11, a non-volatile storage 13, and a memory 16 as a transitory storage region. In addition, the image processing device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. It should be noted that the CPU 11 is an example of a processor according to the present disclosure.

The storage 13 is formed by a hard disk drive (HDD), a solid state drive (SSD), a flash memory, and the like. The image processing program 12A and the learning program 12B installed in the image processing device 10 are stored in the storage 13 as a storage medium. The CPU 11 reads out the image processing program 12A and the learning program 12B from the storage 13, loads the read-out programs into the memory 16, and executes the loaded image processing program 12A and learning program 12B.

In addition, the image processing program 12A and the learning program 12B are stored in a storage device of a server computer connected to the network or a network storage so as to be accessed from the outside and are downloaded and installed in the computer forming the image processing device 10 on demand. Alternatively, the image processing program 12A and the learning program 12B are distributed by being recorded on a recording medium such as a digital versatile disc (DVD) or a compact disc read only memory (CD-ROM) and is then installed onto the computer that constitutes the image processing device 10 from the recording medium.

Figure 3:
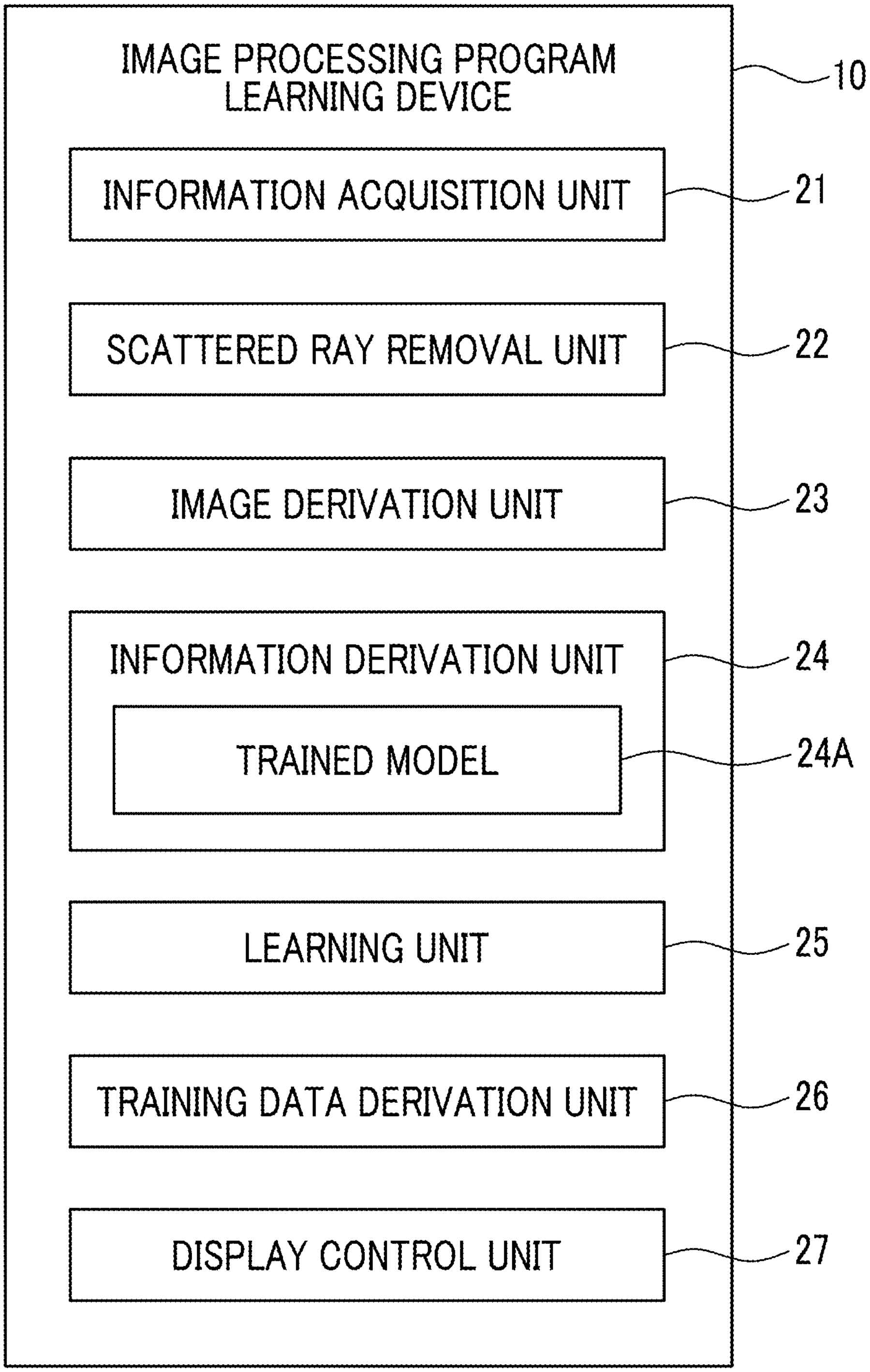
FIG. 3 is a diagram showing a functional configuration of the image processing device and the learning device according to the embodiment of the present disclosure.

Next, a functional configuration of the image processing device and the learning device according to the present embodiment will be described. FIG. 3 is a diagram showing a functional configuration of the image processing device and the learning device according to the present embodiment. As shown in FIG. 3, the image processing device 10 comprises an information acquisition unit 21, a scattered ray removal unit 22, an image derivation unit 23, an information derivation unit 24, a learning unit 25, a training data derivation unit 26, and a display control unit 27. Then, the CPU 11 executes the image processing program 12A to function as an information acquisition unit 21, a scattered ray removal unit 22, an image derivation unit 23, an information derivation unit 24, and a display control unit 27. In addition, the CPU 11 executes the learning program 12B to function as a learning unit 25 and a training data derivation unit 26.

The information acquisition unit 21 causes the imaging apparatus 1 to perform the imaging of the subject H to acquire, from the first and second radiation detectors 5 and 6, the first radiation image G1 and the second radiation image G2 which are frontal images of the vicinity of the crotch of the subject H, for example. In acquiring the first radiation image G1 and the second radiation image G2, imaging conditions are set, such as an imaging dose, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid.

The SOD and the SID are used to calculate a body thickness distribution as described below. It is preferable that the SOD is acquired by, for example, a time of flight (TOF) camera. It is preferable that the SID is acquired by, for example, a potentiometer, an ultrasound distance meter, or a laser distance meter.

The imaging condition may be set by an input from the input device 15 by an operator. The set imaging condition is stored in the storage 13.

In the present embodiment, the first and second radiation images G1 and G2 may be acquired by a program separate from the image processing program 12A and stored in the storage 13. In this case, the information acquisition unit 21 performs the acquisition by reading out the first and second radiation images G1 and G2 stored in the storage 13 from the storage 13 for processing.

In addition, the information acquisition unit 21 acquires training data for training of a neural network, which will be described below, from the image storage system 9 via the network I/F 17. In addition, the three-dimensional image V0 for deriving the training data is acquired as described below.

Here, each of the first radiation image G1 and the second radiation image G2 includes a scattered ray component based on the radiation scattered in the subject H in addition to a primary ray component of the radiation transmitted through the subject H. The scattered ray removal unit 22 removes the scattered ray component from the first radiation image G1 and the second radiation image G2. For example, the scattered ray removal unit 22 may apply the method described in JP2015-043959A to remove the scattered ray component from the first radiation image G1 and the second radiation image G2. In a case where the method described in JP2015-043959A or the like is used, the derivation of the body thickness distribution of the subject H and the derivation of the scattered ray component for removing the scattered ray component are performed at the same time.

Hereinafter, the removal of the scattered ray component from the first radiation image G1 will be described, but the removal of the scattered ray component from the second radiation image G2 can also be performed in the same manner. First, the scattered ray removal unit 22 acquires a virtual model K of the subject H having an initial body thickness distribution T0(*x*,*y*). The virtual model K is data, which virtually represents the subject H, in which the body thickness according to the initial body thickness distribution T0(*x*,*y*) is associated with a coordinate position of each pixel of the first radiation image G1. The virtual model K of the subject H having the initial body thickness distribution T0(*x*,*y*) may be stored in advance in the storage 13. In addition, the initial body thickness distribution T0(*x*, *y*) of the subject H may be calculated based on the SID and the SOD included in the imaging conditions. In this case, the body thickness distribution can be obtained by subtracting the SOD from the SID.

Next, the scattered ray removal unit 22 generates, based on the virtual model K, an image in which an estimated primary ray image obtained by estimating a primary ray image to be obtained by imaging the virtual model K is combined with an estimated scattered ray image obtained by estimating a scattered ray image to be obtained by imaging the virtual model K, as an estimated image obtained by estimating the first radiation image G1 obtained by imaging the subject H.

Next, the scattered ray removal unit 22 corrects the initial body thickness distribution T0(*x*,*y*) of the virtual model K such that a difference between the estimated image and the first radiation image G1 is small. The scattered ray removal unit 22 repeatedly performs the generation of the estimated image and the correction of the body thickness distribution until the difference between the estimated image and the first radiation image G1 satisfies a predetermined end condition. The scattered ray removal unit 22 derives the body thickness distribution in a case where the end condition is satisfied, as the body thickness distribution T(x,y) of the subject H. Further, the scattered ray removal unit 22 subtracts the scattered ray component in a case where the end condition is satisfied from the first radiation image G1 to remove the scattered ray component included in the first radiation image G1. Note that, in the first and second radiation images G1 and G2 in the subsequent processing, the scattered ray components are removed.

Figure 4:
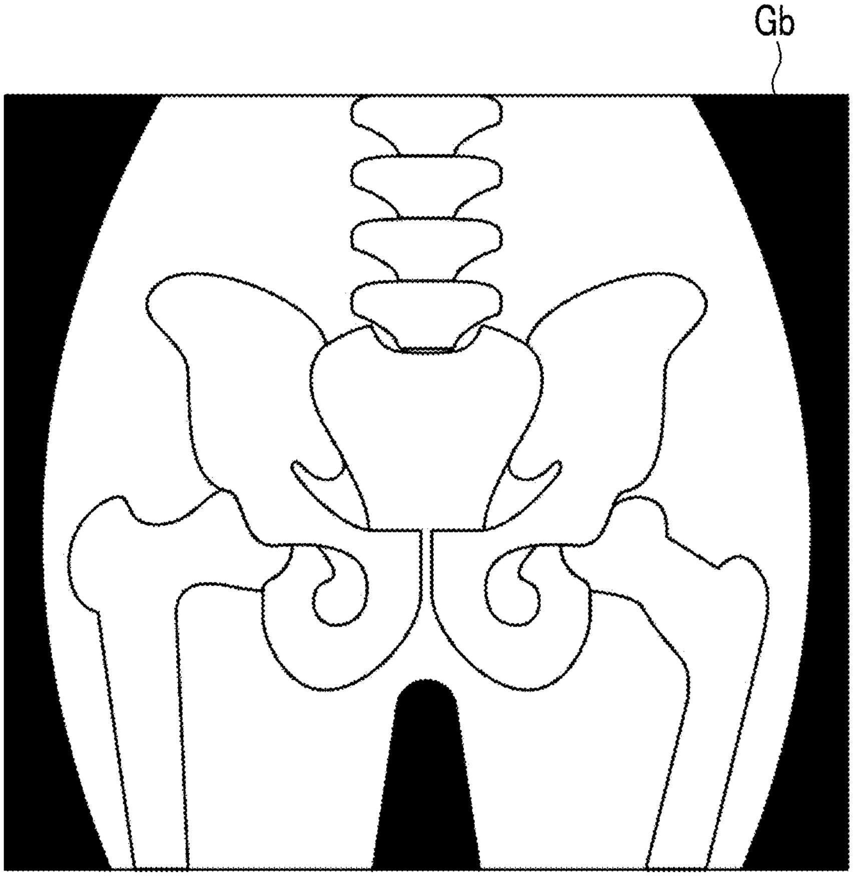
FIG. 4 is a diagram showing a bone part image.

The image derivation unit 23 performs energy subtraction processing to derive a bone part image in which a bone part of the subject H is extracted from the first and second radiation images G1 and G2. The bone part is an example of a structure of the present disclosure, and the bone part image is an example of a structure image of the present disclosure. In a case where the bone part image Gb is derived, the image derivation unit 23 performs weighting subtraction on the first and second radiation images G1 and G2 between respectively corresponding pixels, as shown in Expression (1), to derive the bone part image Gb in which the bone part of the subject H included in each of the radiation images G1 and G2 is extracted, as shown in FIG. 4. In Expression (1), β1 is a weighting coefficient.

$$Gb(x,y) = G1(x,y) - \beta 1 \times G2(x,y) \quad (1)$$

The information derivation unit 24 derives a deviation angle with respect to a reference position of the bone part and composition information at the reference position of the bone part in the bone part image Gb by using the trained model 24A. In the present embodiment, the bone part is a femur, and the composition information is a bone density of the femur. In addition, in the present embodiment, in a case in which the femur on one side of the left and right sides is imaged in the supine position before and after the front surface, the positioning that is generally preferable is set as the reference position. For example, a positioning in which the frontal plane of the pelvis is horizontal, the hip joint portion on the imaging side is aligned with the center of the image receiving surface of the radiation detectors 5 and 6, and the lower limb is in the extension position and the slight internal rotation position is set as the reference position. In a case where the subject H positioned at the reference position is imaged, an incidence angle of the radiation incident on the subject H is set as a reference incidence angle. In the present embodiment, the reference incidence angle is 0 degrees.

The deviation angle with respect to the reference position refers to a deviation of an angle of the incidence angle of the radiation actually incident on the subject H during the imaging of the subject H with respect to a reference incidence angle. The deviation angle is represented by two directions of the zenith angle and the azimuth angle. However, in the present embodiment, the deviation angle means a deviation of an angle around a long axis of the femur.

Here, in a case in which the incidence angle of the radiation with respect to the bone part deviates from the reference incidence angle, the bone part is included in the radiation image in a state of being rotated from the reference position. For example, in a case of the femur, the lower limb is rotated, and the femur is included in the radiation image in a state of internal rotation or external rotation from the reference position.

Figure 5C:
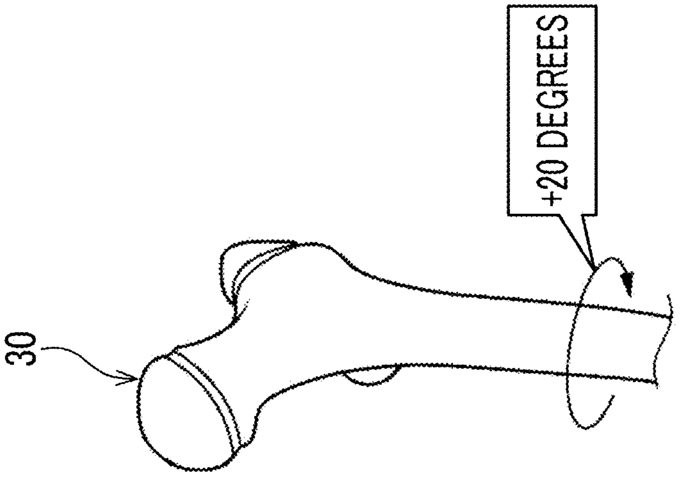
FIGS. 5A to 5C are diagrams for describing a deviation angle of radiation with respect to a femur.
Figure 5B:
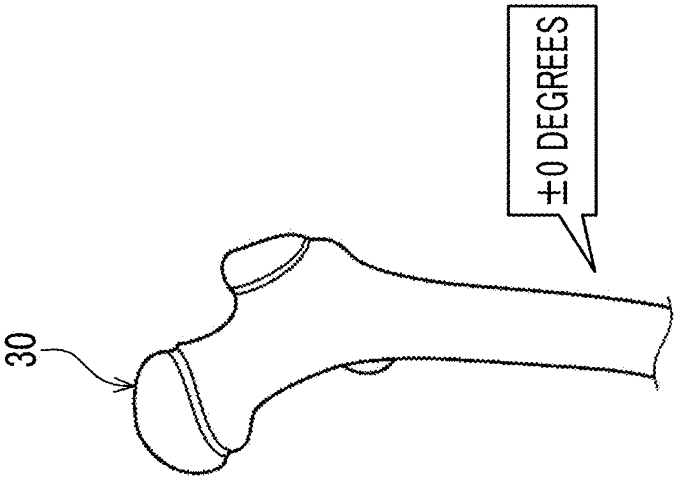
Figure 5A:
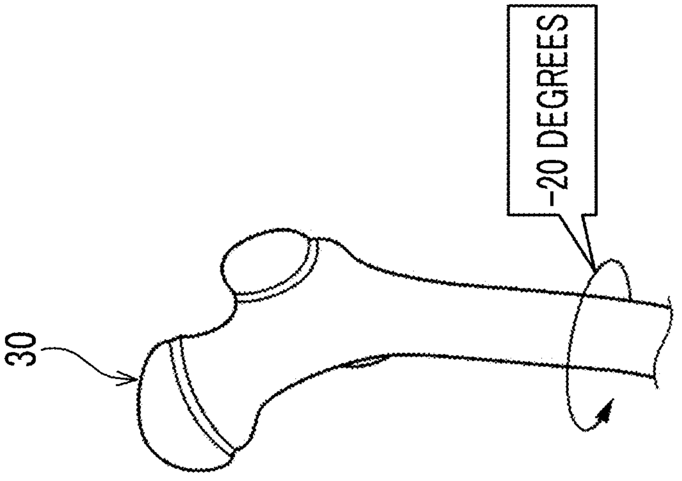

FIGS. 5A to 5C are diagrams for describing a deviation angle of radiation with respect to the femur. In the present embodiment, as shown in FIG. 5B, the incidence angle of the radiation with respect to the femur 30 of the subject H positioned at the reference position is the reference incidence angle. In this case, the deviation angle is 0 degrees.

As shown in FIG. 5A, in a case where the incidence angle of the radiation with respect to the femur 30 deviates from the reference incidence angle, the femur 30 is included in the radiation image in a state of being internally rotated. In this state, a negative value is used as the deviation angle. For example, the deviation angle shown in FIG. 5A is −20 degrees. In addition, in a case in which the incidence angle of the radiation is deviated from the reference incidence angle in a direction opposite to the direction shown in FIG. 5A, the femur 30 is included in the radiation image in a state of being externally rotated. A positive value is used as the deviation angle in this state. For example, the deviation angle shown in FIG. 5C is +20 degrees.

The bone density means the same as the bone mineral content, and the unit is g/cm$^2$. The bone density is derived based on the pixel value of the bone part image Gb. Here, a contrast between the soft part and the bone part in the radiation image is lower as the tube voltage in the radiation source 3 is higher and the energy of the radiation emitted from the radiation source 3 is higher. Further, in a procedure in which the radiation transmits through the subject H, a low-energy component of the radiation is absorbed by the subject H, and beam hardening occurs in which the energy of the radiation is increased. The increase in the energy of the radiation due to the beam hardening is larger as the body thickness of the subject H is larger.

Figure 6:
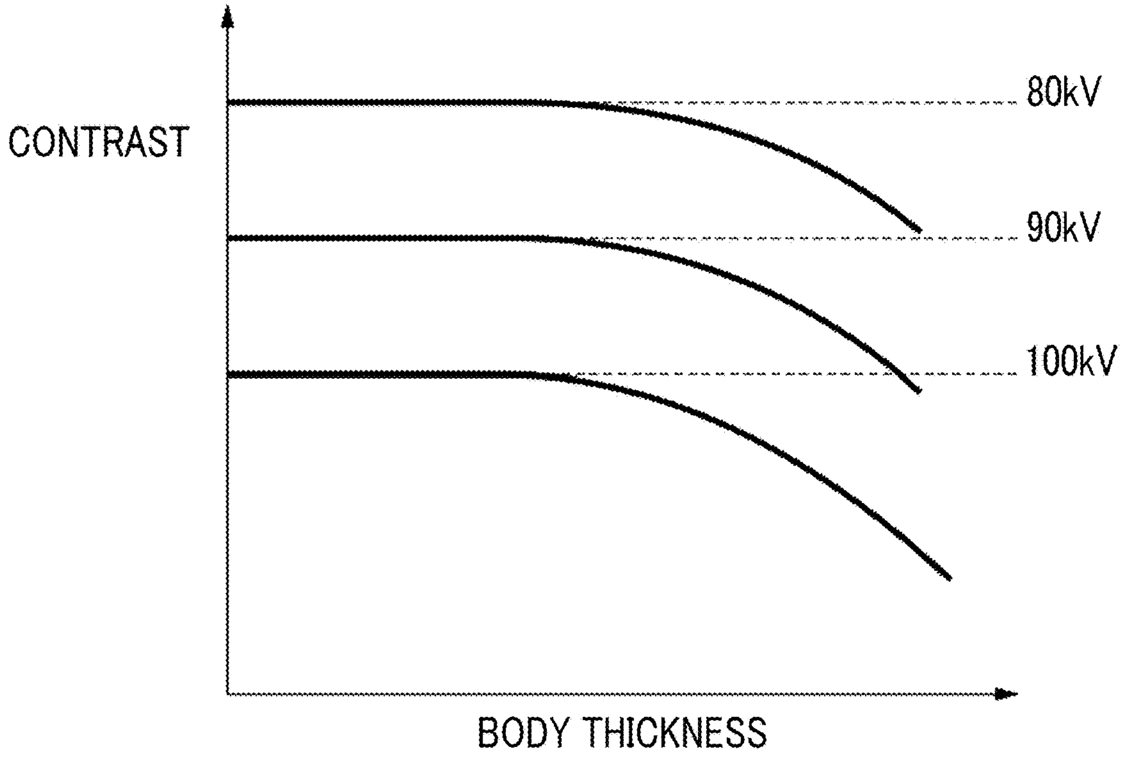
FIG. 6 is a diagram showing a relationship between the contrast of a bone part and a soft part and a body thickness of the subject.

FIG. 6 is a diagram showing a relationship of the contrast between the bone part and the soft part with respect to the body thickness of the subject H. Note that FIG. 6 shows the relationship of the contrast between the bone part and the soft part with respect to the body thickness of the subject H at the three tube voltages of 80 kV, 90 kV, and 100 kV. As shown in FIG. 6, the contrast is lower as the tube voltage is higher. Further, in a case where the body thickness of the subject H exceeds a certain value, the contrast is lower as the body thickness is larger. The contrast between the bone part and the soft part is higher as the pixel value of the bone region in the bone part image Gb is larger. For this reason, the relationship shown in FIG. 6 is shifted to a higher contrast side as the pixel value of the bone region in the bone part image Gb is larger.

The bone density can be derived by correcting the pixel value of the bone part image Gb using a correction coefficient. The correction coefficient is a coefficient for correcting a difference in contrast according to the tube voltage at the time of imaging and a decrease in contrast due to the influence of beam hardening in the bone part image Gb.

Figure 7:
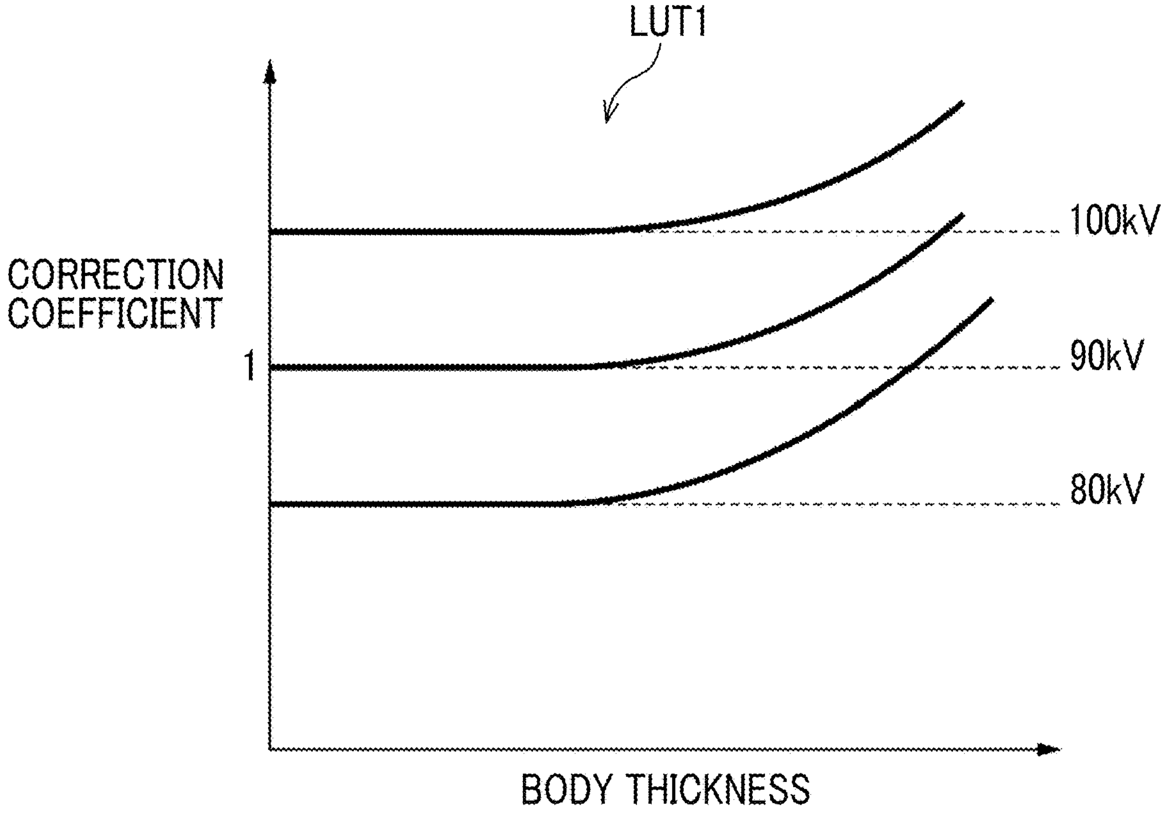
FIG. 7 is a diagram showing an example of a look-up table.

FIG. 7 is a diagram showing a look-up table that defines a relationship between a body thickness and a correction coefficient. In FIG. 7, a look-up table LUT1 in which the standard imaging condition is set to the tube voltage of 90 kV is shown. As shown in FIG. 7, in the look-up table LUT1, as the tube voltage becomes higher and the body thickness of the subject H becomes larger, a larger correction coefficient is set. In the example shown in FIG. 7, since the standard imaging condition is the tube voltage of 90 kV, the correction coefficient is 1 in a case in which the tube voltage is 90 kV and the body thickness is 0. Note that although the look-up table LUT1 is shown in two dimensions in FIG. 7, the correction coefficient differs depending on the pixel value of the bone region. Therefore, the look-up table LUT1 is actually a three-dimensional table to which an axis representing the pixel value of the bone region is added.

In a case of deriving the bone density, a correction coefficient K0($x$, $y$) for each pixel corresponding to the imaging condition including the body thickness distribution T(x, y) of the subject H and the set value of the tube voltage during imaging is extracted from the look-up table LUT1. Then, as shown in the following Expression (2), the bone density D(x,y) (g/cm$^2$) is derived by multiplying each pixel (x,y) of the bone part in the bone part image Gb by the correction coefficient K0($x$,$y$). The bone density D(x,y) derived in this manner represents the pixel value of the bone region included in the radiation image that is acquired by imaging the subject H at the tube voltage of 90 kV, which is the standard imaging condition, and from which the influence of beam hardening is removed.

$$D(x, y) = K0(x, y) \times Gb(x, y) \tag{2}$$

Here, in a case of imaging the subject H, the subject H is positioned such that the femur is at the reference position, but the subject H may move after the positioning. In a case in which the subject H moves, the incidence angle of the radiation with respect to the subject H fluctuates from the reference incidence angle, and the deviation angle of the radiation applied to the femur from the reference position deviates from 0 degrees and becomes a positive or negative value. As a result, the thickness of the femur on the transmission path of the radiation changes. In a case in which the thickness of the femur changes in this way, the bone density derived from the bone part image Gb changes.

Figure 8:
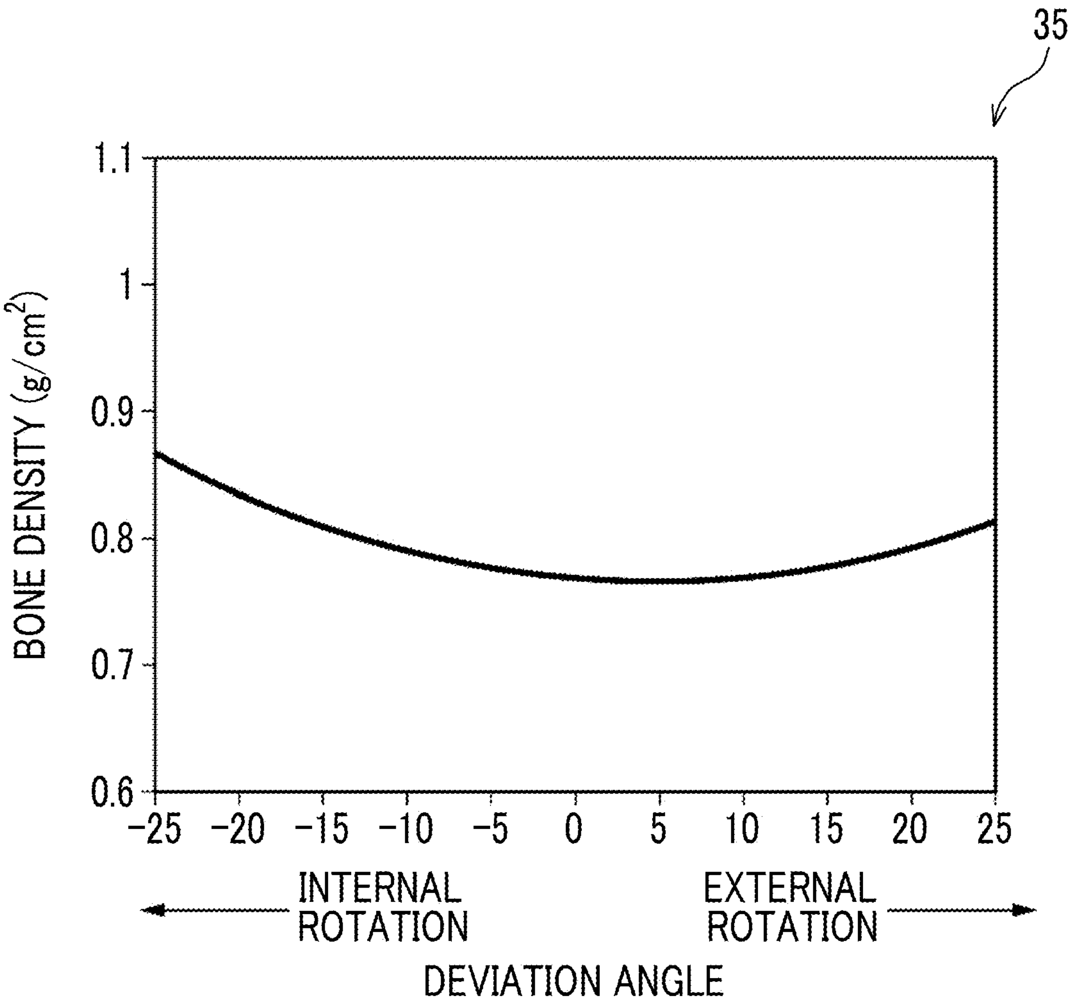
FIG. 8 is a graph showing a relationship between a deviation angle T of radiation with respect to a femur and a bone density.

FIG. 8 is a graph showing a relationship between the deviation angle and the bone density. A graph 35 shown in FIG. 8 shows a relationship between the deviation angle and the bone density measured using the radiation image. In the measurement, for a plurality of bone part images Gb acquired under the same conditions except that the deviation angle is changed to a plurality of predetermined values for the same femur, the bone density converted based on the pixel value for each pixel is derived. In the graph 35, a vertical axis is the bone density, and a horizontal axis is the deviation angle. In the graph 35, a minus sign indicates a deviation angle in a direction included in the radiation image in a case where the femur is in an internal rotation state, and a plus sign indicates a deviation angle in a direction included in the radiation image in a case where the femur is in an external rotation state. As shown in FIG. 8, the bone density changes as the deviation angle changes.

In a case in which the deviation angle with respect to the reference position changes for each capture of the radiation image in this way, the bone density changes. Therefore, there is a concern that the bone density cannot be accurately compared between the radiation images. In addition, in a case where the positioning of the subject is to be performed accurately at the time of imaging, it takes time to perform the imaging.

Therefore, in the present embodiment, the information derivation unit 24 derives the deviation angle of the radiation emitted during the imaging of the bone part included in the bone part image Gb with respect to the reference position and the composition information, that is, the bone density of the bone part using the trained model 24A.

Figure 9:
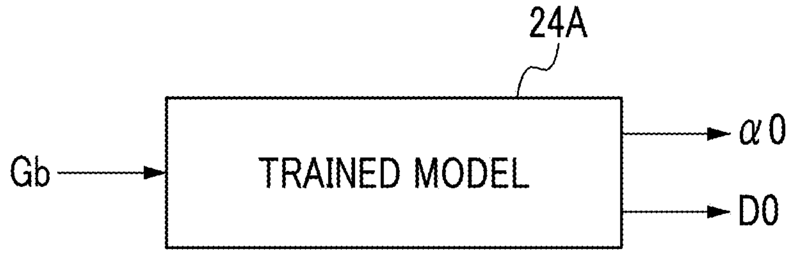
FIG. 9 is a diagram showing an example of a trained model.

FIG. 9 is a diagram schematically showing processing performed by the trained model 24A. The bone part image Gb is input to the trained model 24A. In a case in which the bone part image Gb is input, the trained model 24A outputs the deviation angle α0 and the bone density DO.

Figure 10:
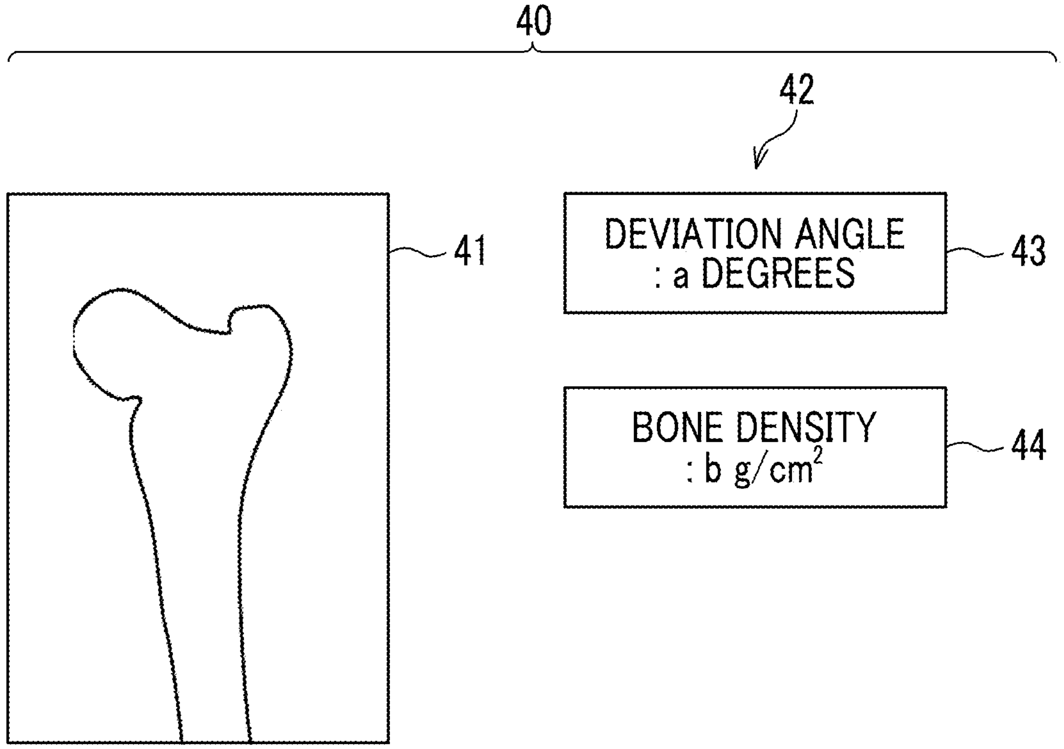
FIG. 10 is a diagram showing training data.

The trained model 24A is constructed by the learning unit 25 training the neural network using the training data. FIG. 10 is a diagram showing training data used for constructing the trained model 24A. As shown in FIG. 10, the training data 40 includes a training bone part image 41 and correct answer data 42, and the correct answer data 42 includes a deviation angle 43 with respect to a reference position of radiation emitted at the time of imaging for the femur included in the training bone part image 41 and a bone density 44 at a reference position of the bone part included in the training bone part image 41. The training bone part image 41 is an example of a training structure image.

Figure 11:
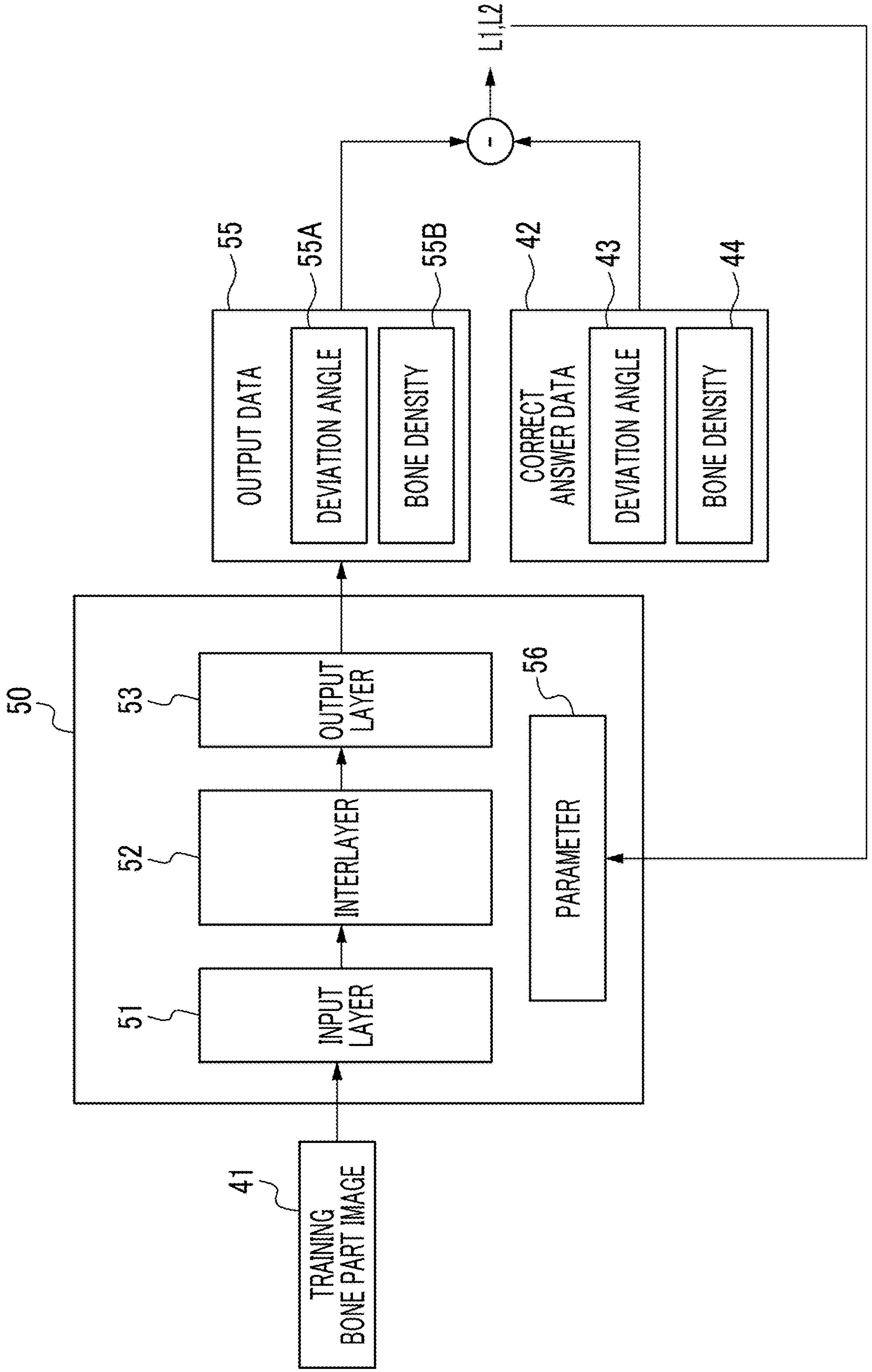
FIG. 11 is a diagram for describing training of the neural network.

The learning unit 25 performs the training of the neural network using a large amount of the training data 40. FIG. 11 is a diagram for describing the training of the neural network 50. As shown in FIG. 11, the neural network 50 includes, for example, an input layer 51, an interlayer 52, and an output layer 53. The interlayer 52 may have a multi-layer structure. In a case of training the neural network 50, the learning unit 25 inputs the training bone part image 41 to the input layer 51 of the neural network 50. Then, the learning unit 25 outputs the deviation angle 55A and the bone density 55B as the output data 55 from the output layer 53 of the neural network 50. Then, the learning unit 25 derives the difference between the deviation angle 55A and the bone density 55B included in the output data 55 and the difference between the deviation angle 43 and the bone density 44 included in the correct answer data 42 as losses L1 and L2, respectively.

The learning unit 25 performs the training of the neural network 50 based on the losses L1 and L2. Specifically, the learning unit 25 adjusts the coefficients of the kernels included in the interlayer 52, the weights of the connection between the layers, and the like (hereinafter, referred to as parameters 56) such that the losses L1 and L2 are reduced. As a method of adjusting the parameter 56, for example, a backpropagation method can be used. The learning unit 25 repeats the adjustment of the parameter 56 until the losses L1 and L2 are equal to or less than a predetermined threshold value. As a result, in a case in which the bone part image Gb is input, the parameter 56 is adjusted so as to output a more accurate deviation angle and bone density, and the trained model 24A is constructed.

In a case in which the bone part image Gb of the subject H is input to the trained model 24A constructed in this way, the trained model 24A outputs the deviation angle α0 and the bone density DO as shown in FIG. 10.

Figure 12:
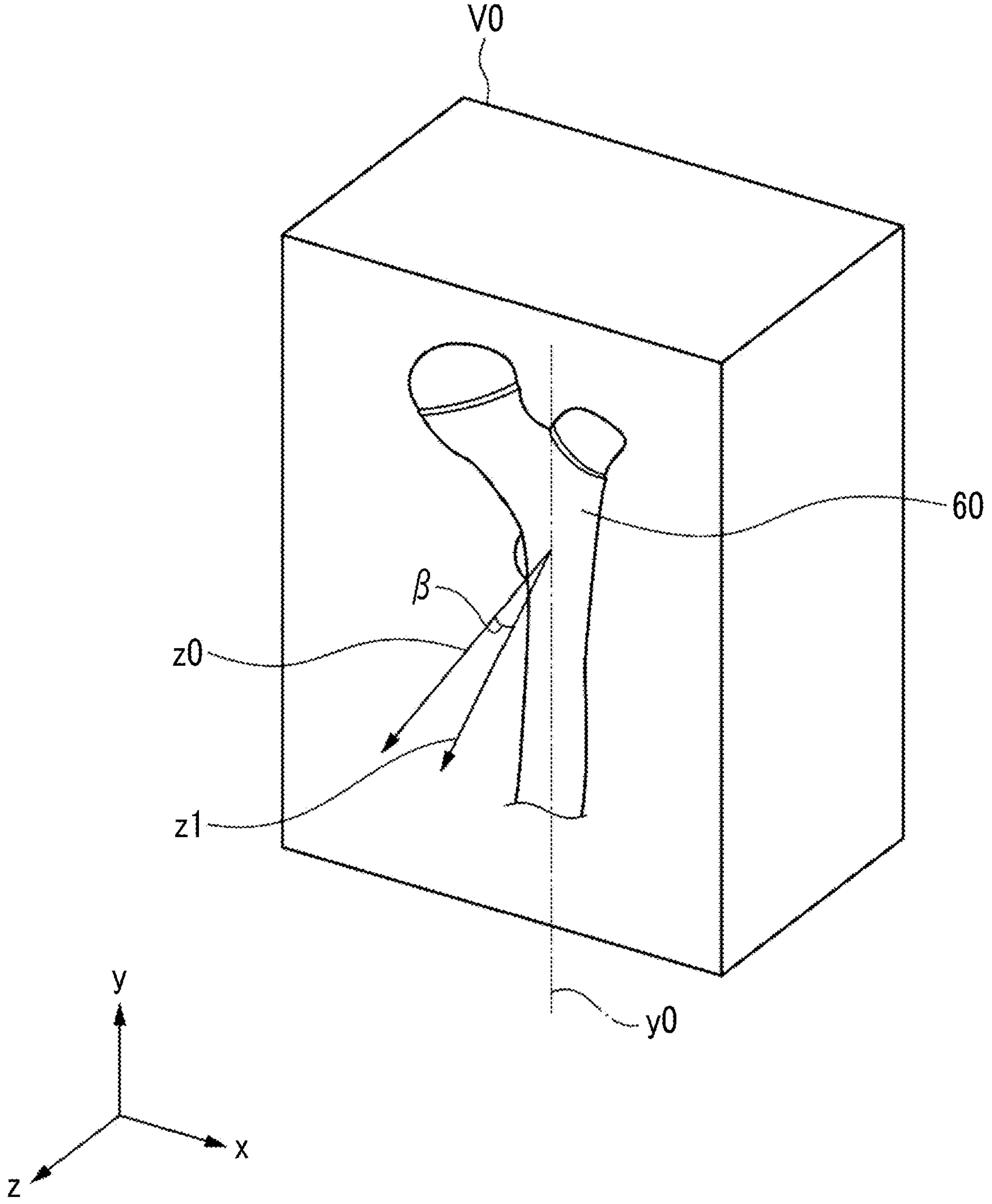
FIG. 12 is a diagram showing derivation of training data.

Here, in the present embodiment, the training data 40 for constructing the trained model 24A is derived by the training data derivation unit 26 using the three-dimensional image V0. Hereinafter, the derivation of the training data 40 will be described. FIG. 12 is a diagram showing derivation of the training data. In FIG. 12, for the sake of description, only the femur 60 is included in the three-dimensional image V0. In addition, in FIG. 12, the long axis y0 of the femur 60 is included in the three-dimensional image V0 so as to extend in the y-axis direction. In addition, in a case in which the three-dimensional image V0 is projected in the z-axis direction, that is, the three-dimensional image V0 is projected onto the xy plane to derive the projection image of the femur, the three-dimensional image V0 is disposed such that the femur is positioned at the reference position. In FIG. 12, a projection direction in the z-axis direction is indicated by z0. In this case, the deviation angle is 0 degrees.

The training data derivation unit 26 segments the three-dimensional image V0 into a bone part and a soft part. In the present embodiment, the three-dimensional image V0 is a CT image, and since the CT values of the bone part and the soft part are significantly different from each other, the bone part and the soft part can be segmented by threshold value processing or the like.

Here, it is considered to project the femur 60 included in the three-dimensional image V0 onto a plane perpendicular to a certain projection direction. In a case where N voxels are arranged in the projection direction, the thickness td(x, y) of the femur is represented by the following Expression (3). In Expression (3), s is a size of a voxel of the three-dimensional image V0.

[Expression 1]

$$td(x, y) = \sum_{i=1}^{N} s_i \tag{3}$$

The training data derivation unit 26 derives the thickness of the femur 60 in each pixel of a projection image (hereinafter, referred to as a reference projection image Pb) in which the femur 60, that is, the bone part is projected onto the xy plane, by using Expression (3). Next, the training data derivation unit 26 derives a volumetric bone density (unit: g/cm$^3$) from the average CT value CTm in the projection direction of the femur 60. An average CT value CTm(x, y) in the projection direction can be derived by the following Equation (4). In Expression (4), CTi is a CT value of a voxel arranged in the projection direction. In addition, (x, y) representing the pixel position of the projection image is omitted in Expression (4).

[Expression 2]

$$CTm = \frac{(CT_1 + CT_2 + \ldots + CT_N)}{N} = \frac{1}{N}\sum_{i=1}^{N} CT_i \tag{4}$$

Figure 13:
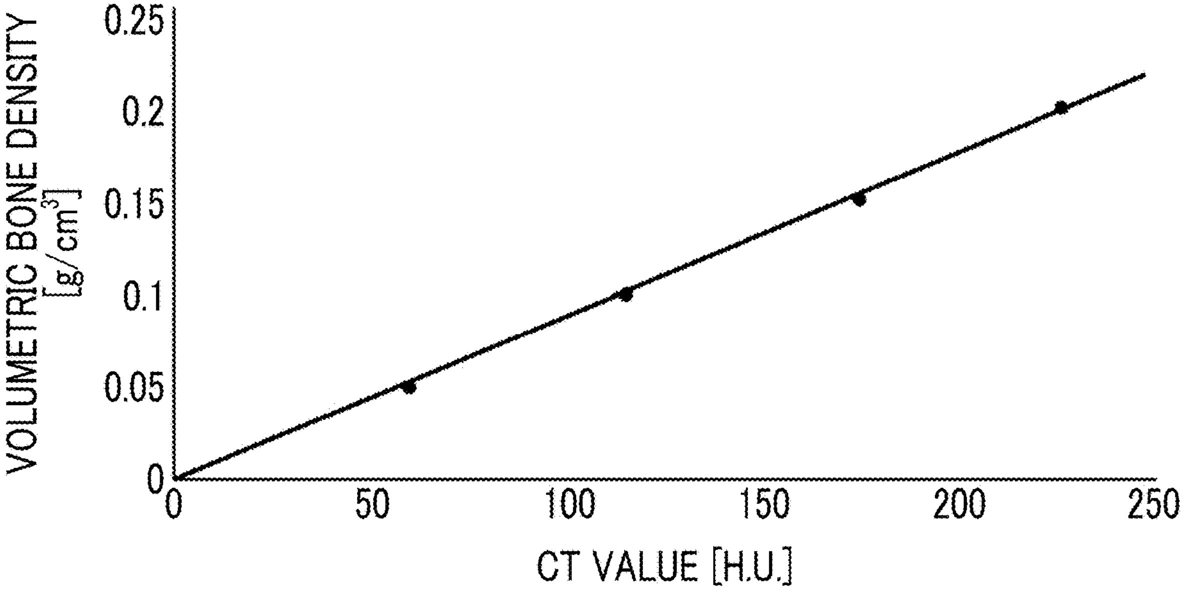
FIG. 13 is a diagram showing a conversion table between a CT value and a volumetric bone density.

Here, the CT value is a relative value to a radiation attenuation coefficient of water, and the bone density can be derived from the attenuation of the radiation by the bone. Since the CT image is a three-dimensional image, the bone density obtained from the CT image is the volumetric bone density. In addition, the volumetric bone density has a substantially proportional relationship with the CT value. Therefore, the conversion table shown in FIG. 13 is created in advance using a bone sample having a known volumetric bone density, and the average CT value (unit: H.U.) is converted into the volumetric bone density Dt ($g/cm^3$). Then, the training data derivation unit 26 derives the area bone density Ds (=Dt×td, the unit is $g/cm^2$) in the reference projection image by multiplying the derived volumetric bone density Dt by the thickness td. The derived area bone density Ds is the bone density 44 included in the correct answer data 42 of the training data 40.

Figure 14:
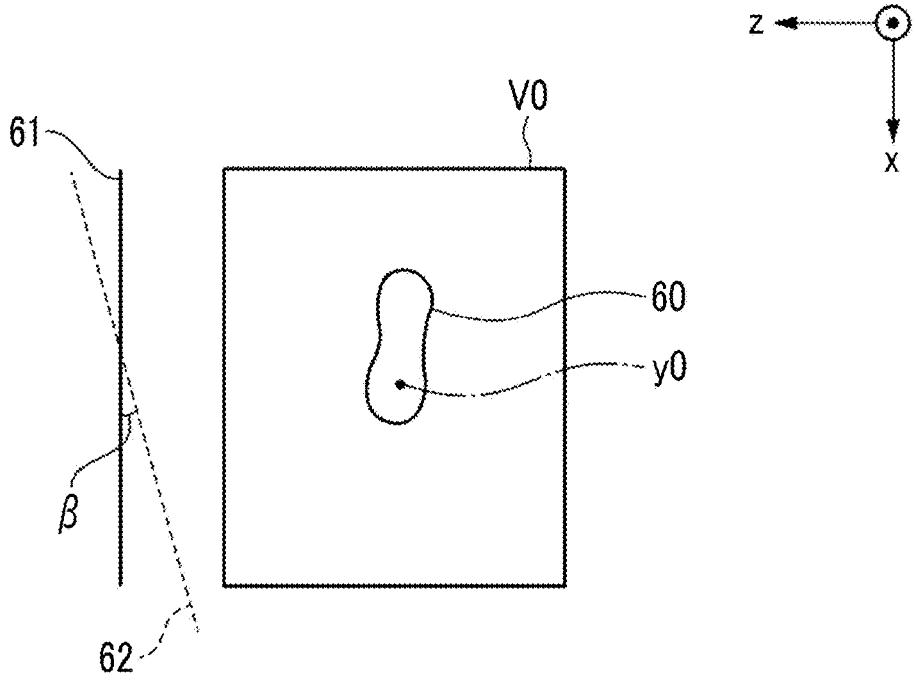
FIG. 14 is a diagram for describing setting of a projection plane.

On the other hand, as shown in FIG. 14, the training data derivation unit 26 sets a projection plane 62 obtained by rotating the projection plane (reference projection plane 61, that is, the xy plane) from which the reference projection image is derived by an angle β about the y-axis. Then, the femur 60 included in the three-dimensional image V0 is projected onto the projection plane 62 to derive the training bone part image 41. In this case, the projection direction of the three-dimensional image V0 is the z1 direction shown in FIG. 12. In addition, the angle β is the deviation angle 43 included in the correct answer data 42.

As described above, the training data derivation unit 26 derives the training bone part image 41, the deviation angle 43, and the bone density 44. It should be noted that a large number of training data 40 can be derived by using the three-dimensional image V0 of the subject having different ages, genders, physiques, and bone densities and changing the angle R in various ways.

The training data derivation unit 26 may derive the training data 40 by measuring the rotation angle of the femur as the deviation angle and deriving the bone density using Expression (2) for the bone part image Gb derived from the first and second radiation images G1 and G2.

Figure 15:
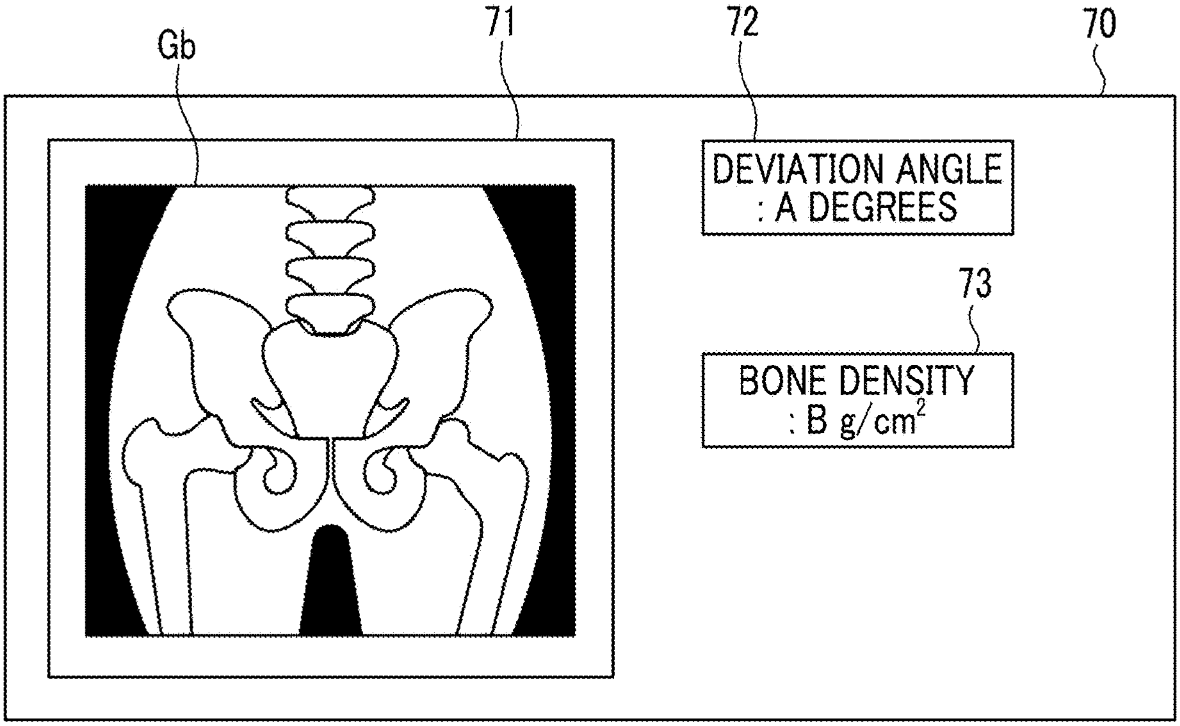
FIG. 15 is a diagram showing a display screen.

The display control unit 27 displays the deviation angle α0 and the bone density DO derived by the information derivation unit 24 on the display 14. FIG. 15 is a diagram showing a display screen of the deviation angle and the bone density. As shown in FIG. 15, the display screen 70 includes an image display region 71. The bone part image Gb is displayed in the image display region. In addition, on the display screen 70, a deviation angle 72 (A degree) and a bone density 73 ($Bg/cm^2$) are displayed on the right side of the image display region 71.

Figure 16:
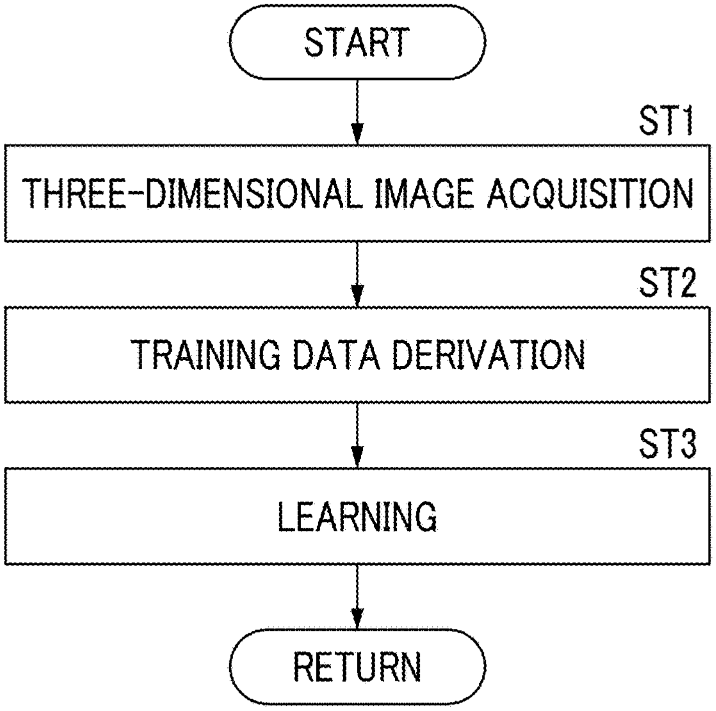
FIG. 16 is a flowchart showing learning processing performed in the present embodiment.

Next, processing performed in the present embodiment will be described. FIG. 16 is a flowchart showing learning processing performed in the present embodiment. First, the information acquisition unit 21 acquires the three-dimensional image V0 from the image storage system 9 (step ST1), and the training data derivation unit 26 derives the training data 40 from the three-dimensional image V0 (step ST2). Then, the learning unit 25 inputs the training bone part image 41 included in the training data 40 to the neural network 50 to output the deviation angle and the bone density, and trains the neural network 50 using the losses L1 and L2 based on the difference from the correct answer data 42 (step ST3), and returns to step ST1. The learning unit 25 further repeats the processing of steps ST1 to ST3 until the losses L1 and L2 are a predetermined threshold value, and ends the learning. The learning unit 25 may repeat the learning a predetermined number of times and end the learning. Therefore, the learning unit 25 constructs the trained model 24A.

Figure 17:
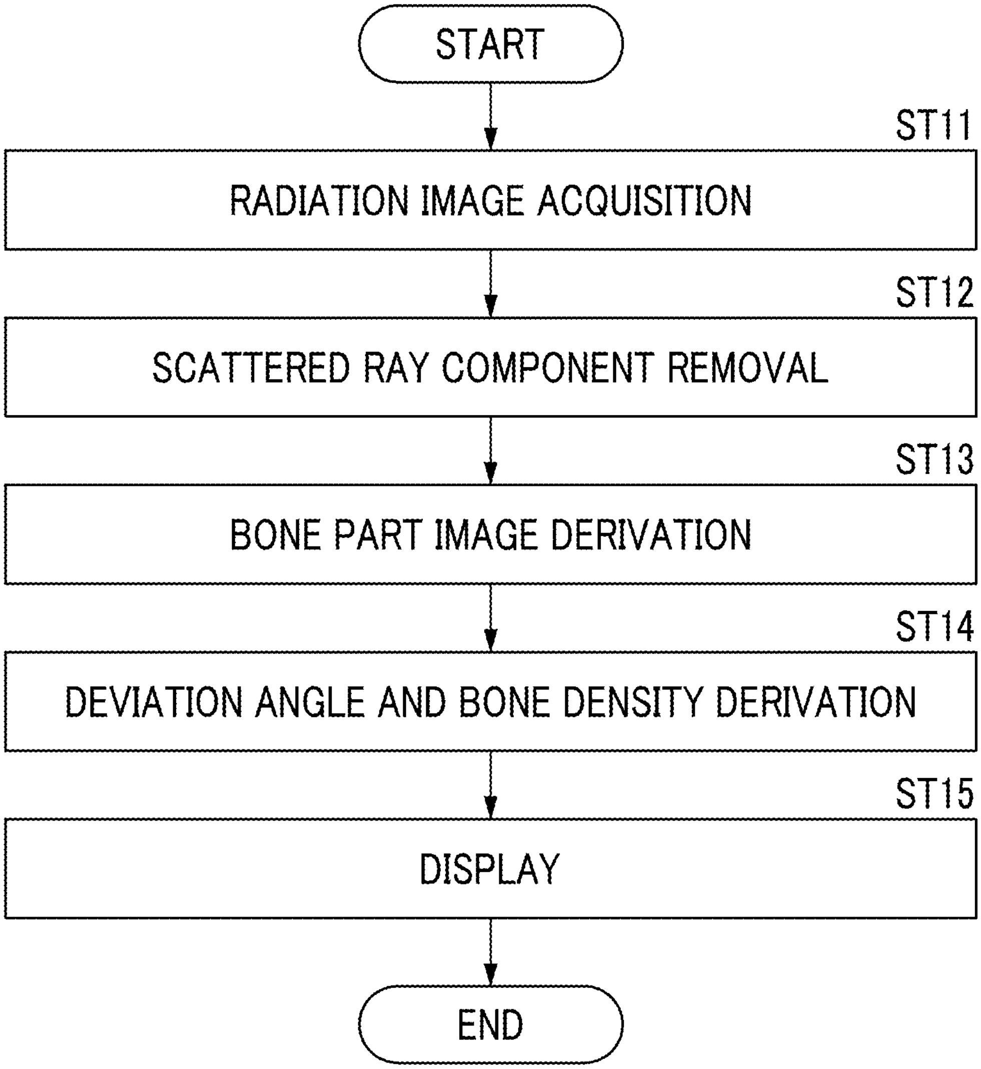
FIG. 17 is a flowchart of image processing performed in the present embodiment.

Next, image processing in the present embodiment will be described. FIG. 17 is a flowchart showing image processing in the present embodiment. Note that the first and second radiation images G1 and G2 are acquired by the imaging and stored in the storage 13. In a case where an instruction to start the processing is input from the input device 15, the information acquisition unit 21 acquires the first and second radiation images G1 and G2 from the storage 13 (radiation image acquisition; step ST11). Then, the scattered ray removal unit 22 removes the scattered ray components from the first and second radiation images G1 and G2 (step ST12). In addition, the image derivation unit 23 derives a bone part image Gb in which the bone part of the subject H is extracted from the first and second radiation images G1 and G2 (step ST13).

Subsequently, the information derivation unit 24 derives the deviation angle and the bone density at the reference position from the bone part image Gb (step ST14). Then, the display control unit 27 displays the derived deviation angle and bone density (step ST15), and the processing is ended.

As described above, in the present embodiment, by using the trained model 24A that outputs the estimation result of the deviation angle with respect to the reference position of the radiation emitted during the imaging for the bone part included in the bone part image Gb and bone density at the reference position of the bone part, the deviation angle with respect to the reference position of the bone part included in the bone part image Gb and the bone density at the reference position of the bone part are derived, by input of the bone part image Gb. Therefore, the deviation angle and the bone density can be accurately derived regardless of the positioning of the subject.

In the above-described embodiment, the femur is used as the bone part, but the present disclosure is not limited thereto. For example, the deviation angle with respect to the reference position of the vertebra or the lumbar vertebra and the bone density at the reference position may be derived for the vertebra or the lumbar vertebra among the vertebrae.

In addition, in the above-described embodiment, the bone part is targeted as the structure, and the deviation angle and the composition information with respect to the reference position are derived, but the present disclosure is not limited to this. For various structures included in the human body, such as a soft part in the subject, fat included in the soft part, muscle included in the soft part, and a metal, such as titanium, embedded in the human body, the deviation angle with respect to the reference position and the composition information at the reference position may be derived. In addition to the density of the structure, the thickness may be derived as the composition information. In addition, both the density and the thickness may be derived as the composition information.

The processing in a case where the soft part is used as the structure will be described below. In a case where the soft part is the structure, the trained model may be constructed to output the deviation angle with respect to the reference position of the soft part and the thickness of the soft part as the composition information from the soft part image. However, since the soft tissue of the human body is not a rigid body, it is difficult to accurately obtain the deviation angle unlike the bone part.

Figure 18:
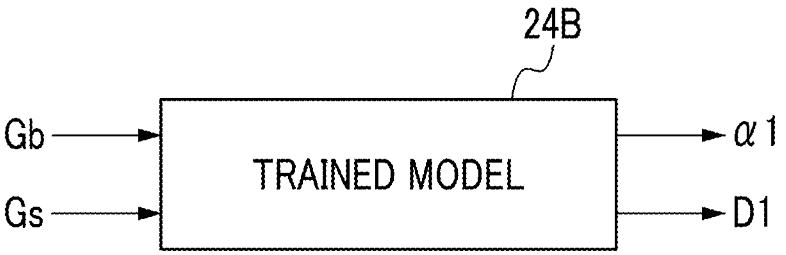
FIG. 18 is a diagram showing another example of the trained model.

On the other hand, the deviation angle of the radiation with respect to the soft part is equal to the deviation angle of the radiation with respect to the bone part. Therefore, in order to obtain the deviation angle of the soft part and the composition information (thickness), a trained model is constructed to derive both the soft part image Gs and the bone part image Gb and derive the deviation angle derived from the bone part image Gb as the deviation angle for the soft part. FIG. 18 is a diagram showing a trained model constructed to derive a deviation angle and a thickness of a soft part from a soft part image and a bone part image. As shown in FIG. 18, in a case in which the soft part image Gs and the bone part image Gb are input, the trained model 24B derives the deviation angle α1 for the soft part and the thickness D1 of the soft part.

Further, in the embodiment described above, the scattered ray components are removed from the first and second radiation images G1 and G2 by the scattered ray removal unit 22, but the present disclosure is not limited to this. The bone part image Gb may be derived without removing the scattered ray component. In this case, the scattered ray removal unit 22 is not required.

In addition, in the above-described embodiment, the image processing device includes the learning device, but the present disclosure is not limited thereto. The image processing device and the learning device may be separately provided, and the trained model constructed by the learning device may be applied to the image processing device.

In addition, in the embodiment described above, the first and second radiation images G1 and G2 are acquired by the one-shot method in a case in which the energy subtraction processing is performed, but the present disclosure is not limited to this. The first and second radiation images G1 and G2 may be acquired by a so-called two-shot method in which imaging is performed twice by using only one radiation detector. In a case of the two-shot method, there is a possibility that a position of the subject H included in the first radiation image G1 and the second radiation image G2 deviates due to a body movement of the subject H. Therefore, in the first radiation image G1 and the second radiation image G2, it is preferable to perform the processing according to the present embodiment after registration of the subject is performed.

Further, in the embodiment described above, the image processing is performed by using the radiation image acquired by the system that images the first and second radiation images G1 and G2 of the subject H by using the first and second radiation detectors 5 and 6, it is needless to say that the technology of the present disclosure can be applied to even in a case where the first and second radiation images G1 and G2 are acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case where the first and second radiation images G1 and G2 are acquired by using the accumulative phosphor sheet.

In addition, in the above-described embodiment, the bone part image Gb and the soft part image Gs are derived by the energy subtraction processing, but the present disclosure is not limited thereto. For example, the bone part image Gb may be derived by emphasizing the bone part in one radiation image acquired by using only one radiation detector.

In addition, the bone part image Gb and the soft part image Gs may be derived by the following method. Hereinafter, other embodiments of the structure image derivation will be described. The first and second radiation images G1 and G2 acquired by the information acquisition unit 21 include a region of the subject H and a direct radiation region obtained by directly irradiating the radiation detectors 5 and 6 with radiation. A soft region and a bone region are included in the region of the subject H. A soft part component of a human body includes muscle, fat, blood, and water. Here, the non-fat tissue including blood and moisture is treated as muscle.

The soft regions of the first and second radiation images G1 and G2 include only the soft part component of the subject H. The bone regions of the first and second radiation images G1 and G2 are actually regions in which the bone part component and the soft part component are mixed.

Figure 19:
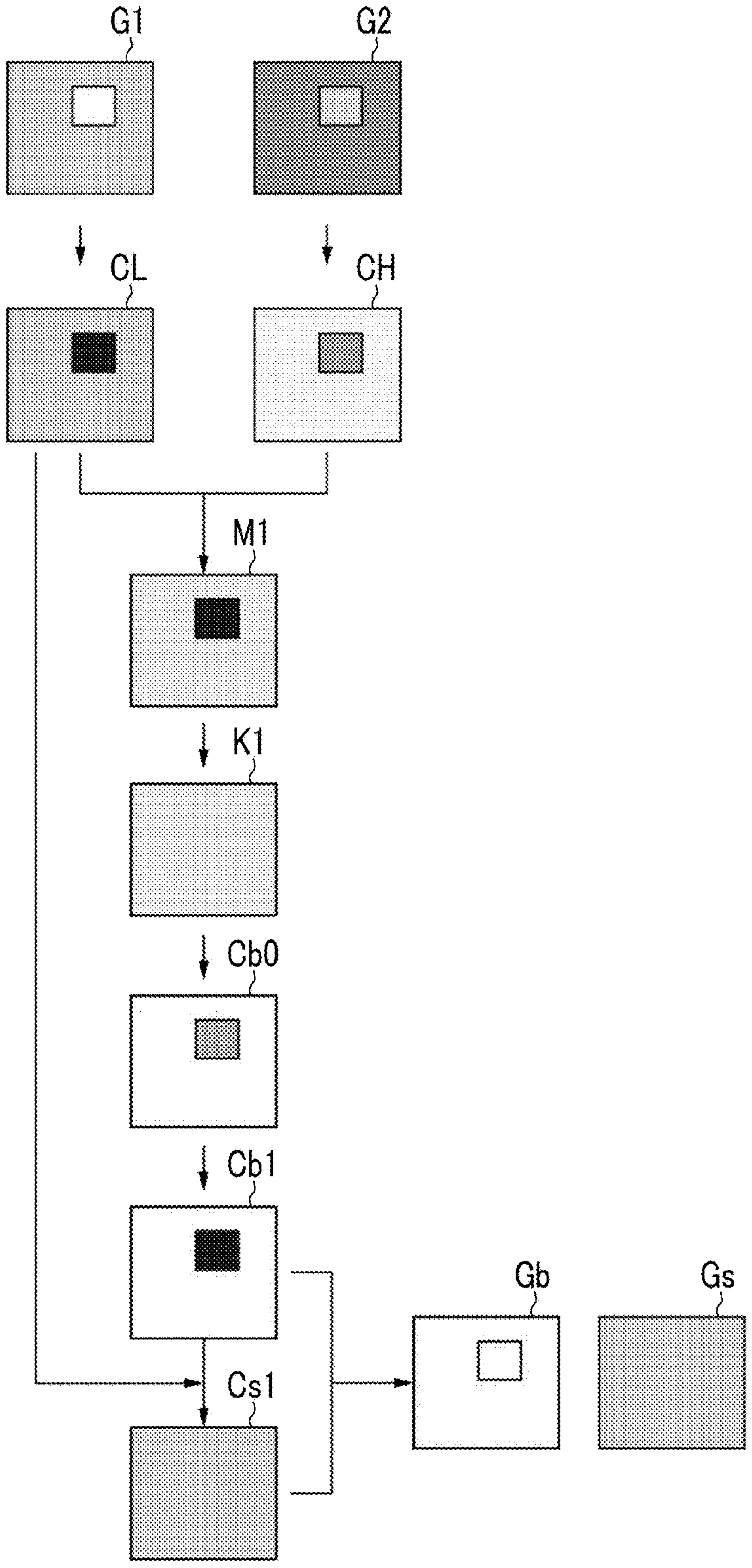
FIG. 19 is a diagram schematically showing processing performed in the first embodiment of the structure image derivation.

Hereinafter, a first other embodiment of the structure image derivation will be described. Hereinafter, four other embodiments of the structure image derivation will be described, and each of which will be referred to as a first to fourth embodiment. FIG. 19 is a diagram schematically showing processing performed in the radiation image processing device according to the first embodiment of the structure image derivation. Note that, in FIG. 19, in order to simplify the description, the first radiation image G1 and the second radiation image G2 do not include the direct radiation region, and include a rectangular bone region in the soft region.

In the first embodiment of the structure image derivation, the image derivation unit 23 specifies the bone region and the soft region in the first radiation image G1 or the second radiation image G2. For this reason, the image derivation unit 23 derives an attenuation characteristic related to the attenuation of the radiation in at least the region of the subject H of the first radiation image G1 or the second radiation image G2, and specifies the soft region and the bone region based on the attenuation characteristic in the region of the subject H. In the first embodiment of the structure image derivation, the image derivation unit 23 derives the first attenuation image CL and the second attenuation image CH representing the attenuation amount of the radiation by the subject H from each of the first radiation image G1 and the second radiation image G2, and derives an attenuation ratio, which is a ratio between the corresponding pixels of the first attenuation image CL and the second attenuation image CH, as the attenuation characteristic.

Here, a pixel value of the first attenuation image CL represents the attenuation amount of the low-energy radiation due to the subject H, and a pixel value of the second attenuation image CH represents the attenuation amount of the high-energy radiation due to the subject H. The first attenuation image CL and the second attenuation image CH are derived from the first radiation image G1 and the second radiation image G2 by Expression (5) and Expression (6). In the expression (5), Gd1 is the pixel value of the direct radiation region in the first radiation image G1, and, in the expression (6), Gd2 is the pixel value of the direct radiation region in the second radiation image G2.

$$CL(x,y) = Gd1 - G1(x,y) \quad (5)$$

$$CH(x,y) = Gd2 - G2(x,y) \quad (6)$$

Next, the image derivation unit 23 derives an attenuation ratio map representing the attenuation ratio of radiation between the first radiation image G1 and the second radiation image G2. Specifically, an attenuation ratio map M1 is derived by deriving a ratio between the corresponding pixels of the first attenuation image CL and the second attenuation image CH by Expression (7)

$$M1(x,y)=CL(x,y)/CH(x,y) \quad (7)$$

Here, in the first radiation image G1 and the second radiation image G2, the attenuation ratio of the region including only the soft part component is smaller than the attenuation ratio of the region including the bone part component. Therefore, the image derivation unit 23 compares the attenuation ratios of the respective pixels of the attenuation ratio map M1, specifies a region consisting of the pixel in which the attenuation ratio is larger than a predetermined threshold value as the bone region, and specifies a region other than the bone region as the soft region. Note that the image derivation unit 23 may compare the attenuation ratio between each pixel of the attenuation ratio map M1 with the surrounding pixels, and may specify the pixel having a larger attenuation ratio than surrounding pixels as the pixel in the bone region.

The image derivation unit 23 derives a characteristic of a first component related to the attenuation of the radiation based on the first radiation image G1 and the second radiation image G2 in the first component region including only the first component in the first radiation image G1 or the second radiation image G2, that is, in the soft region. In addition, the image derivation unit 23 derives the characteristic of the first component in the second component region, that is, the bone region, based on the characteristic of the first component derived in the soft region around the bone region. In the present embodiment, the image derivation unit 23 derives the attenuation ratio between the first radiation image G1 and the second radiation image G2 as the characteristic of the first component.

On the other hand, for the bone region, the attenuation ratio of the soft region around the bone region is interpolated to derive the characteristic of the first component for the bone region, that is, the attenuation ratio. Note that, instead of the interpolation, a median value of the attenuation ratio of the soft region in the attenuation ratio map M1, an average value thereof, or a value thereof that is a predetermined ratio from the small attenuation ratio side may be derived as the attenuation ratio for the bone region.

As a result, the image derivation unit 23 derives the characteristic of the first component for the region of the subject H of the first radiation image G1 or the second radiation image G2. In the first embodiment, the characteristic of the first component is the attenuation ratio of the soft region. In the first embodiment, the derived characteristic of the first component is used as a soft part removal coefficient K1 for removing the soft part in a case of deriving the bone part image.

The image derivation unit 23 derives a first component image in which the first component is emphasized and a second component image in which the second component is emphasized, based on the characteristic of the first component in a region of the subject H in the first radiation image G1 or the second radiation image G2. Specifically, the image derivation unit 23 derives a soft part image Gs in which the soft part component is emphasized and a bone part image Gb in which the bone part component is emphasized.

In the first embodiment of the structure image derivation, first, the image derivation unit 23 derives an initial second component attenuation image in which the second component is emphasized, that is, an initial bone part attenuation image in which the bone part is emphasized, based on the first attenuation image CL, the second attenuation image CH, and the soft part removal coefficient K1, which is the characteristic of the first component. Specifically, the image derivation unit 23 derives an initial bone part attenuation image Cb0 by Expression (8).

$$Cb0(x,y)=CL(x,y)-CH(x,y)\times K1(x,y) \quad (8)$$

Here, as the pixel value of the bone region of the initial bone part attenuation image Cb0 derived as described above, there are the pixel value obtained by replacing the attenuation amount of the bone part with the attenuation amount of the soft part by assuming that the soft part corresponding to the thickness of the bone part is present, and the pixel value representing a difference from an actual attenuation amount of the bone part. Therefore, a contrast is low with respect to the bone part attenuation image that is originally desired to be derived. In a case in which the bone part attenuation image having such a low contrast is used, in a case in which a soft part attenuation image is derived by subtracting the bone part attenuation image from the first attenuation image CL or the second attenuation image CH as will be described below, the bone part component cannot be removed satisfactorily.

Therefore, in the first embodiment, the image derivation unit 23 derives a bone part attenuation image Cb1 by matching a contrast of the initial bone part attenuation image Cb0 with a contrast of the first attenuation image CL or the second attenuation image CH. In the first embodiment, the contrast of the initial bone part attenuation image Cb0 is matched with the contrast of the first attenuation image CL. Therefore, the image derivation unit 23 converts the contrast of the initial bone part attenuation image Cb0 by multiplying the initial bone part attenuation image Cb0 by a contrast conversion coefficient. Then, a correlation between a difference value $\Delta$CL derived by subtracting the initial bone part attenuation image Cb0 after the contrast conversion from the first attenuation image CL and the initial bone part attenuation image Cb0 is derived. Then, the contrast conversion coefficient is determined so that the correlation is minimized, and the determined contrast conversion coefficient is multiplied by the initial bone part attenuation image Cb0 to derive the bone part attenuation image Cb1.

Note that a table representing the contrast conversion coefficient in which the contrast of the initial bone part attenuation image Cb0 and a body thickness are associated with each other may be created in advance. In this case, the bone part attenuation image Cb1 may be derived by deriving the body thickness of the subject H by the measurement or the like, deriving the contrast conversion coefficient with reference to the table from the contrast and the body thickness of the initial bone part attenuation image Cb0, and converting the initial bone part attenuation image Cb0 by using the derived contrast conversion coefficient.

Then, the image derivation unit 23 derives a soft part attenuation image Cs1 by subtracting the bone part attenuation image Cb1 from the first attenuation image CL by Expression (9).

$$Cs1(x,y)=CL(x,y)-Cb1(x,y) \quad (9)$$

Further, the image derivation unit 23 derives the bone part image Gb and the soft part image Gs by Expression (10) and Expression (11).

$$Gb(x,y)=Gd1(x,y)-Cb1(x,y) \quad (10)$$

$$Gs(x,y)=Gd2(x,y)-Cs1(x,y) \quad (11)$$

Figure 20:
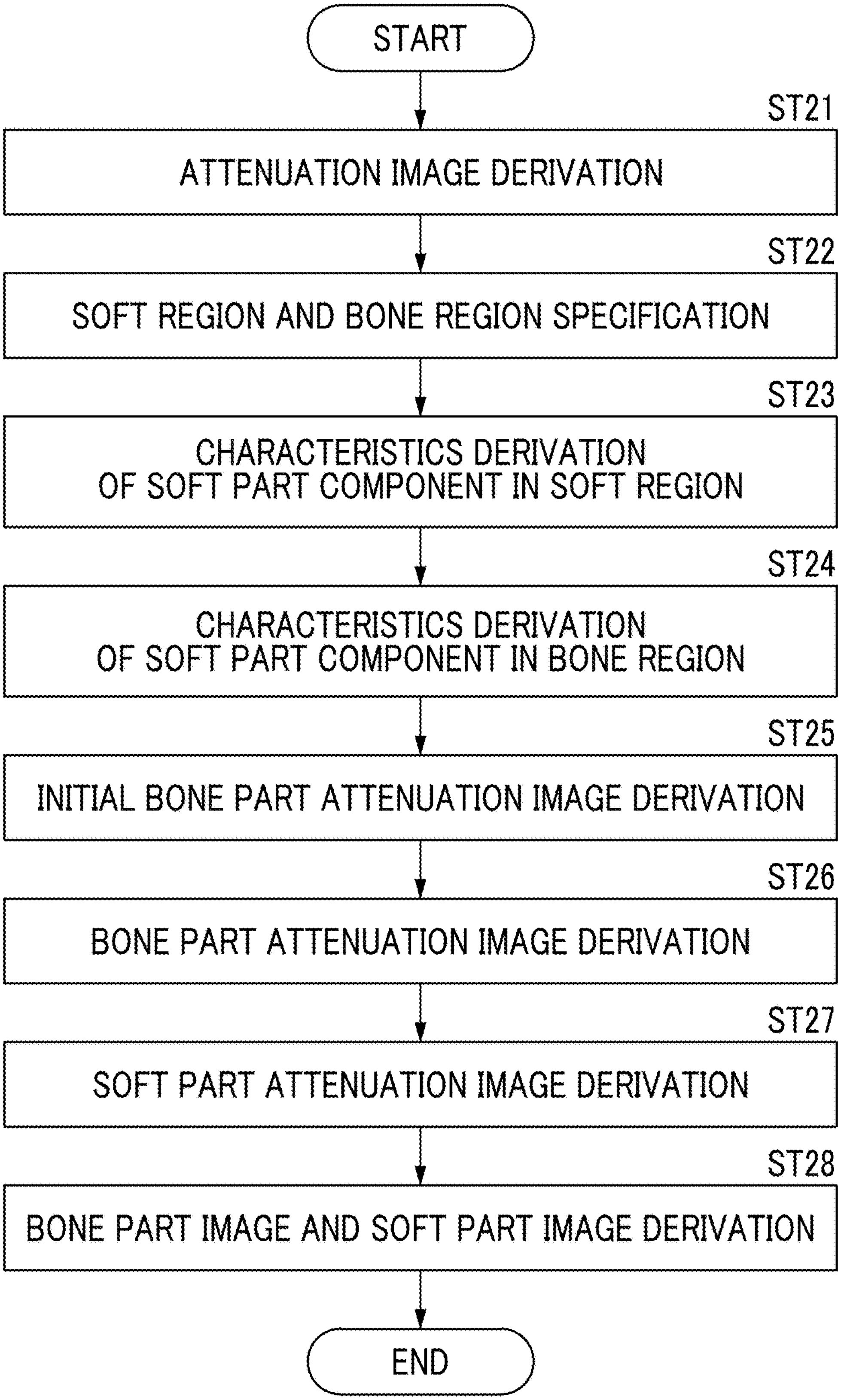
FIG. 20 is a flowchart showing processing performed in the first embodiment of the structure image derivation.

Next, processing performed in the first embodiment of the structure image derivation will be described. FIG. 20 is a flowchart showing processing performed in the first embodiment of the structure image derivation. It is assumed that the first and second radiation images are acquired by the information acquisition unit 21 and the scattered ray component is removed by the scattered ray removal unit 22. First, the image derivation unit 23 derives the first attenuation image CL and the second attenuation image CH from the first radiation image G1 and the second radiation image G2 (attenuation image derivation: step ST21), and specifies the soft region including only the soft part component and the bone region including the bone part in the first attenuation image CL or the second attenuation image CH (step ST22). Next, the image derivation unit 23 derives the characteristics (attenuation ratio) of the soft part component related to the attenuation of the radiation image in the soft region (step ST23). Subsequently, the image derivation unit 23 derives the characteristics of the soft part component in the bone region (step ST24).

Next, the image derivation unit 23 derives the initial bone part attenuation image Cb0 (step ST25), and derives the bone part attenuation image Cb1 by converting the contrast of the initial bone part attenuation image Cb0 (step ST26). Further, the image derivation unit 23 derives the soft part attenuation image Cs1 by subtracting the bone part attenuation image Cb1 from the first attenuation image CL (step ST27). Subsequently, the image derivation unit 23 derives the bone part image Gb and the soft part image Gs by Expression (10) and Expression (11) described above (step ST28), and ends the processing.

As described above, in the first embodiment of the structure image derivation, the attenuation ratio in the bone region including the bone part component in the first radiation image G1 or the second radiation image G2 is derived based on the attenuation ratio of the soft part component derived in the soft region around the bone region. Then, the soft part image Gs in which the soft part component is emphasized and the bone part image Gb in which the bone part component is emphasized are derived based on the attenuation ratio in at least the region of the subject H in the first radiation image G1 or the second radiation image G2. Therefore, the attenuation ratio of the soft part component in the bone region can be derived accurately, and as a result, the soft part image Gs and the bone part image Gb in which the soft part component and the bone part component are separated accurately can be derived.

In addition, in the first embodiment of the structure image derivation, the first attenuation image CL and the second attenuation image CH representing the attenuation amounts of the radiation are derived from the first radiation image G1 and the second radiation image G2, and the soft part image Gs and the bone part image Gb are derived by using the first attenuation image CL and the second attenuation image CH. Therefore, in a case in which the derived attenuation amount is used as the soft part removal coefficient K1 for removing the soft part component, the soft part component can be removed satisfactorily by Expression (8). Therefore, it is possible to derive the soft part image Gs and the bone part image Gb in which the soft part component and the bone part component are separated accurately.

Figure 21:
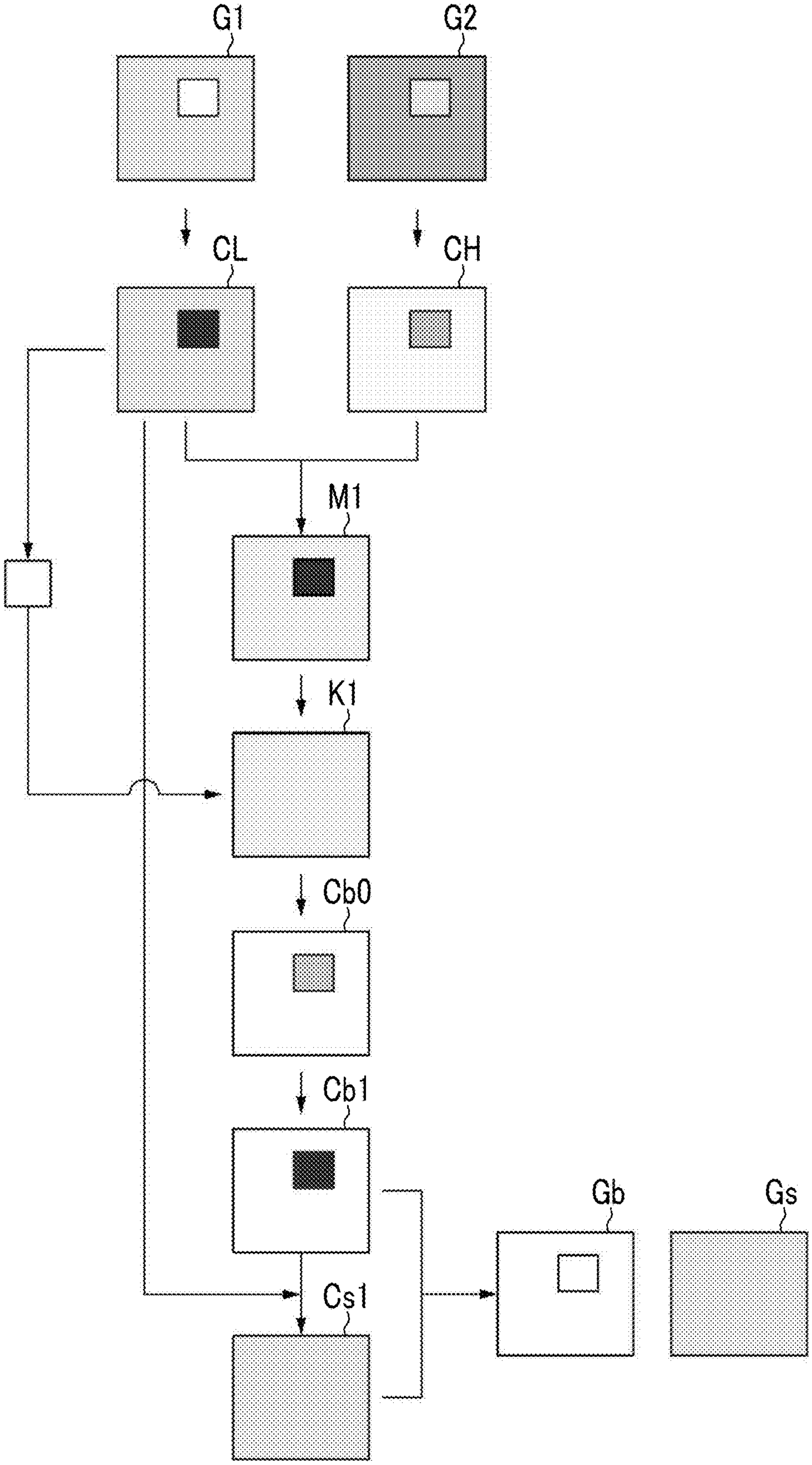
FIG. 21 is a diagram schematically showing processing performed by the radiation image processing device according to the second embodiment of the structure image derivation.

Next, a second embodiment of the structure image derivation will be described. FIG. 21 is a diagram schematically showing processing performed in the second embodiment of the structure image derivation. As shown in FIG. 21, the image derivation unit 23 detects the bone region from the first attenuation image CL or the second attenuation image CH. Note that the bone region may be detected from the first radiation image G1 or the second radiation image G2. For this reason, in the second embodiment, the image derivation unit 23 uses a trained model constructed by subjecting a neural network to machine learning so as to detect the bone region from the radiation image or the attenuation image. In this case, the trained model is constructed to detect the bone region by learning the bone region based on the pixel value of the radiation image or the attenuation image.

On the other hand, in the radiation image or the attenuation image, the pixel value of the bone region and the pixel value of the soft region including only the soft part component are significantly different from each other. Therefore, the bone region may be detected from the radiation image or the attenuation image by performing the threshold value processing on the radiation image or the attenuation image. In addition, in the radiation image or the attenuation image, the shape of the bone region is specified by the difference between the pixel value of the bone region and the pixel value of the soft region including only the soft part component. Therefore, the bone region may be detected from the radiation image or the attenuation image by the template matching using the shape of the bone region according to a part of the subject H included in the radiation image or the attenuation image.

Then, in the second embodiment, the image derivation unit 23 derives the attenuation ratio of the soft part component in the bone region specified based on the pixel value of the radiation image or the attenuation image as described above. Since the processing after deriving the attenuation ratio of the soft part component in the bone region is the same as the processing of the first embodiment of the structure image derivation, the detailed description thereof will be omitted here.

Note that, in the first and second embodiments of the structure image derivation, the initial bone part attenuation image Cb0, the bone part attenuation image Cb1, and the soft part attenuation image Cs1 are derived by using the first attenuation image CL, the second attenuation image CH, and the soft part removal coefficient K1, and then the bone part image Gb and the soft part image Gs are derived. However, the present disclosure is not limited to this. The bone part image Gb and the soft part image Gs may be derived by Expression (12) and Expression (13) by using the first radiation image G1, the second radiation image G2, and the soft part removal coefficient K1.

$$Gb(x,y)=G1(x,y)-K1(x,y)\times G2(x,y) \quad (12)$$

$$Gs(x,y)=G1(x,y)-Gb(x,y) \quad (13)$$

Next, a third embodiment of the structure image derivation will be described. In the first embodiment described above of the structure image derivation, the attenuation ratio of the soft part component is derived as the characteristic of the first component. However, the third embodiment is different from the first embodiment in that a soft part attenuation coefficient, which is the attenuation coefficient of the low-energy radiation and the high-energy radiation due to the soft part component is derived as the characteristic of the first component.

Figure 22:
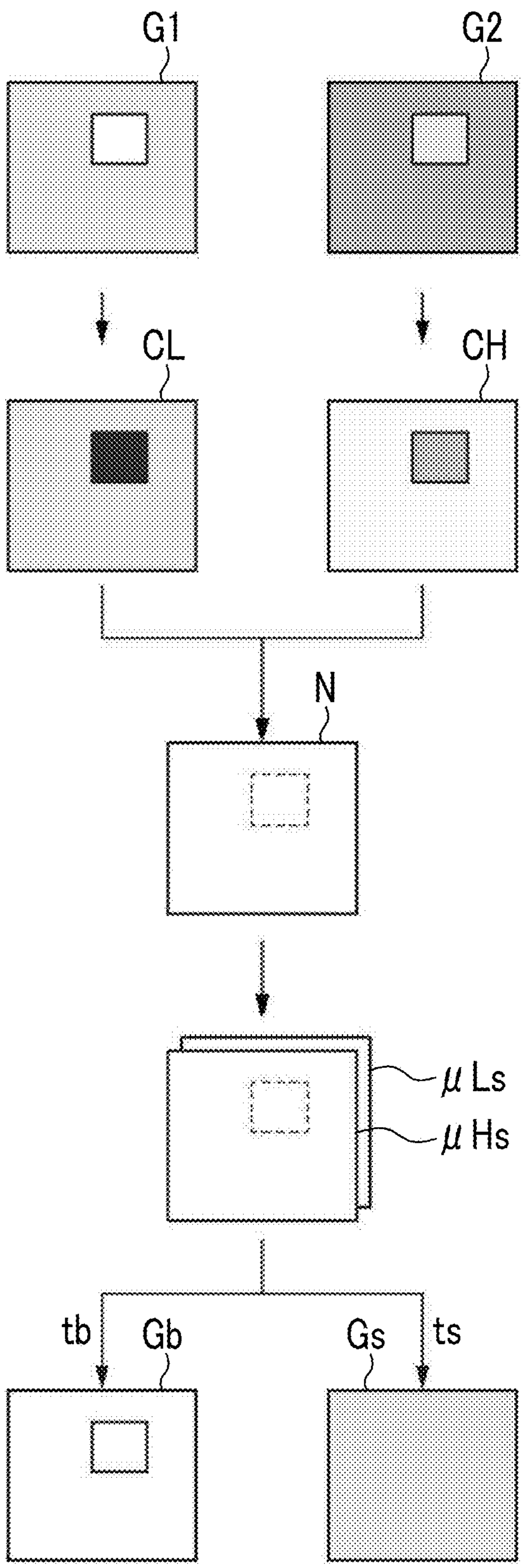
FIG. 22 is a diagram schematically showing processing performed by the radiation image processing device according to the third embodiment of the structure image derivation.

FIG. 22 is a diagram schematically showing processing performed in the third embodiment of the structure image derivation. In the third embodiment, since the processing until the image derivation unit 23 derives the first attenuation image CL and the second attenuation image CH is the same as the processing in the first and second embodiments, the detailed description thereof will be omitted.

In the third embodiment, the image derivation unit 23 derives a ratio of the fat at each pixel position of the first and second radiation images G1 and G2 by using the attenuation coefficients of the fat and the muscle for each of the high-energy radiation and the low-energy radiation. Then, the image derivation unit 23 specifies the bone region and the soft region based on the derived fat ratio.

Here, the attenuation amount of the radiation due to the subject H is determined depending on the thicknesses of the soft part and the bone part and a radiation quality (whether high energy or low energy). Therefore, in a case in which the attenuation coefficient representing an attenuation rate per unit thickness is, attenuation amounts CLO and CHO of the radiation at each pixel position in each of the low-energy image and the high-energy image can be represented by Expression (14) and Expression (15). In Expression (14) and Expression (15), ts is a thickness of the soft part, tb is a thickness of the bone part, μLs is the soft part attenuation coefficient of the low-energy radiation, μLb is a bone part attenuation coefficient of the low-energy radiation, JHS is the soft part attenuation coefficient of the high-energy radiation, and THB is the bone part attenuation coefficient of the high-energy radiation.

$$CL0=\mu Ls(ts,tb)\times ts+\mu Lb(ts,tb)\times tb \quad (14)$$

$$CH0=\mu Hs(ts,tb)\times ts+\mu Hb(ts,tb)\times tb \quad (15)$$

In Expression (14) and Expression (15), the attenuation amount CLO of the low-energy image corresponds to the pixel value of the first attenuation image CL, and the attenuation amount CHO of the high-energy image corresponds to the pixel value of the second attenuation image CH. Therefore, Expression (14) and Expression (15) are represented by Expression (16) and Expression (17). Note that all of Expression (14) to Expression (17) represent a relationship between the first attenuation image CL and the second attenuation image CH in each pixel, but (x,y) representing the pixel position is omitted.

$$CL=\mu Ls(ts,tb)\times ts+\mu Lb(ts,tb)\times tb \quad (16)$$

$$CH=\mu Hs(ts,tb)\times ts+\mu Hb(ts,tb)\times tb \quad (17)$$

By solving Expression (16) and Expression (17) with the thickness ts of the soft part and the thickness tb of the bone part as variables, the thickness ts of the soft part and the thickness tb of the bone part can be derived. In order to solve Expression (16) and Expression (17), the soft part attenuation coefficients μLs and μHs and the bone part attenuation coefficients μLb and μHb for each of the low-energy radiation and the high-energy radiation are necessary. Here, since there is no difference in the composition of the bone part according to the subject H, the bone part attenuation coefficients μLb and μHb according to the thickness ts of the soft part and the thickness tb of the bone part can be prepared in advance.

On the other hand, the soft part cannot be prepared in advance because the muscle and the fat are mixed in a complicated manner and the ratio of the muscle and the fat differs according to the subject H. Therefore, in the third embodiment of the structure image derivation, the image derivation unit 23 derives the soft part attenuation coefficient μLs for the low-energy radiation and the soft part attenuation coefficient μHs for the high-energy radiation by using the first attenuation image CL and the second attenuation image CH. Hereinafter, the derivation of the soft part attenuation coefficients μLs and μHs will be described.

Figure 23:
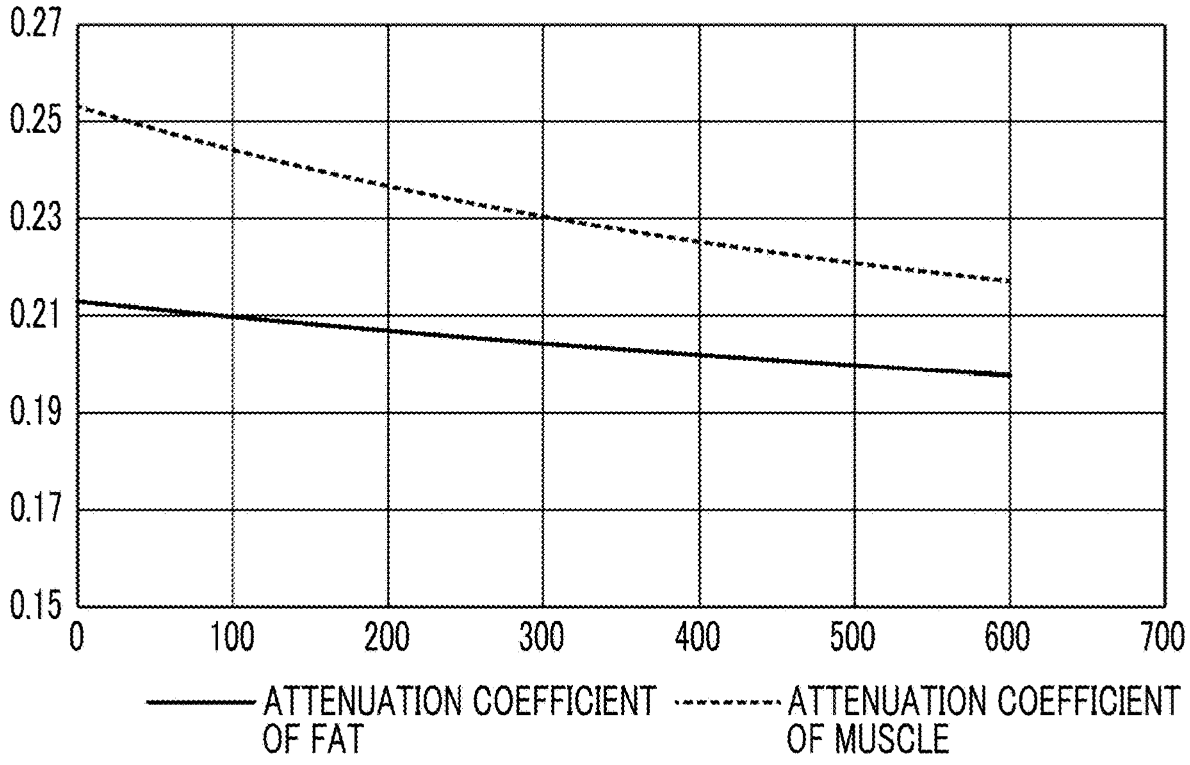
FIG. 23 is a diagram showing attenuation coefficients of fat and muscle.

In the third embodiment of the structure image derivation, the soft part attenuation coefficient is derived on the assumption that, among the compositions constituting the soft part, the composition having the highest density is the muscle, the composition having a lower density is the fat, and a mixed composition in which the fat and the muscle are mixed has an intermediate value of both attenuation coefficients. First, the image derivation unit 23 calculates provisional soft part attenuation coefficients μ0Ls and μ0Hs for each of the low-energy radiation and the high-energy radiation by setting the ratio of the fat at each pixel position to N % and performing weighting addition of the attenuation coefficient of the fat and the attenuation coefficient of the muscle at a ratio of N:100−N while sequentially increasing N from zero. It should be noted that, in a case in which the fat and the muscle overlap each other, the attenuation coefficient is changed due to the influence of the radiation quality hardening of the component (usually the fat) present on the radiation source 3 side, but, in the present embodiment, the influence of the radiation quality hardening is not taken into consideration. Therefore, N %, which is the ratio of the fat used in the present embodiment, does not match the actual body fat percentage of the subject H. The processing is based on the assumption that the actual soft part attenuation coefficient is a value between the attenuation coefficient of the fat and the attenuation coefficient of the muscle shown in FIG. 23.

Next, the image derivation unit 23 calculates a body thickness TN in a case in which the ratio of the fat is N % by Expression (18) from the pixel value of the first attenuation image CL and the provisional soft part attenuation coefficient μ0Ls for the low-energy image. In this case, the body thickness TN is calculated on the assumption that the pixel including the bone part is also composed of only the soft part.

$$TN(x,y)=CL(x,y)/\mu 0Ls(x,y) \quad (18)$$

Next, the image derivation unit 23 calculates an attenuation amount CHN1 of the high-energy radiation according to Expression (19) from the body thickness TN calculated by Expression (18) and the provisional soft part attenuation coefficient μ0Hs for the high-energy radiation. Then, the second attenuation image CH is subtracted from the attenuation amount CHN1 by Expression (20) to calculate a difference value ΔCH.

$$CHN1(x,y)=TN(x,y)\times\mu 0Hs(x,y) \quad (19)$$

$$\Delta CH(x,y)=CHN1(x,y)-CH(x,y) \quad (20)$$

A case in which the difference value ΔCH is a negative value means that the provisional soft part attenuation coefficients μ0Ls and μ0Hs are smaller than a correct answer soft part attenuation coefficient, that is, closer to the fat. A case in which the difference value ΔCH is a positive value means that the provisional soft part attenuation coefficients μ0Ls and μ0Hs are closer to the muscle. The image derivation unit 23 calculates the provisional soft part attenuation coefficients μ0Ls and μ0Hs for all the pixels of the first attenuation image CL and the second attenuation image CH while changing N such that the difference value ΔCH approaches zero. Then, N in a case in which the difference value ΔCH is 0 or equal to or smaller than a predetermined threshold value is determined as the ratio of the fat for the pixel. In addition, the image derivation unit 23 determines the provisional soft part attenuation coefficients μ0Ls and μ0Hs in the calculation of the determined ratio N of the fat as the soft part attenuation coefficients μLs and μHs. Note that, the ratio N of the fat need only be increased in a case in which the difference value ΔCH is a negative value, and the ratio N of the fat need only be decreased in a case in which the difference value ΔCH is a positive value.

Here, at the pixel of the region including the bone part component in the first radiation image G1 and the second radiation image G2, the ratio of the fat is a value close to 0 or a negative value. In a case in which the subject H is a human being, the ratio of the fat cannot be 0 or a negative value. Therefore, the image derivation unit 23 specifies the region consisting of the pixel at which the ratio N of the fat in the first radiation image G1 and the second radiation image G2 is a value close to 0 (for example, a value smaller than the predetermined threshold value) or a negative value, as the bone region in the first radiation image G1 and the second radiation image G2. In addition, the image derivation unit 23 specifies a region other than the bone region in the first radiation image G1 and the second radiation image G2 as a soft region.

In the third embodiment, the image derivation unit 23 derives the soft part attenuation coefficients μLs and μHs as the characteristics of the first component. On the other hand, the image derivation unit 23 derives the soft part attenuation coefficients μLs and μHs in the bone region by interpolating the soft part attenuation coefficient of the soft region around the bone region. Note that, instead of the interpolation, a median value of the soft part attenuation coefficients μLs and μHs in the soft region, an average value thereof, or a value thereof that is a predetermined ratio from the small attenuation coefficient side may be derived as the soft part attenuation coefficients μLs and μHs for the bone region. As a result, the image derivation unit 23 derives the characteristic of the first component for at least the region of the subject H of the first radiation image G1 or the second radiation image G2.

In the third embodiment, the image derivation unit 23 derives the soft part image Gs in which the soft part component is emphasized and the bone part image Gb in which the bone part component is emphasized. In the third embodiment, the thickness ts of the soft part and the thickness tb of the bone part are derived based on the soft part attenuation coefficients μLs and μHs derived by the image derivation unit 23 and the bone part attenuation coefficients μLb and μHb derived in advance, and the soft part image Gs and the bone part image Gb are derived based on the thickness ts of the soft part and the thickness tb of the bone part, which are derived.

Expression (16) and Expression (17) are used to derive the thickness ts of the soft part and the thickness tb of the bone part. As described above, the image derivation unit 23 derives the thickness ts of the soft part and the thickness tb of the bone part by solving Expression (16) and Expression (17) with the thickness ts of the soft part and the thickness tb of the bone part as variables. It should be noted that the thickness ts of the soft part and the thickness tb of the bone part, which are derived, are derived for each pixel of the first attenuation image CL and the second attenuation image CH, but, in the following description, (x,y) representing the pixel position will be omitted.

First, the image derivation unit 23 calculates a thickness ts0 of the soft part in a case in which the thickness tb of the bone part=0 is by Expression (17). In a case of tb=0 and ts=ts0, CH=μHs(ts,0)×ts0+μHb(ts0,0)×0=μHs(ts0,0)×ts0, and thus ts0 is calculated by Expression (21). In addition, the image derivation unit 23 calculates a thickness tb0 of the bone part in a case in which the thickness ts of the soft part is 0 by Expression (17). In a case of ts=0 and tb=tb0, CH=μHs(0,tb0)×0+μHb(0,tb0)×tb0, and thus tsb is calculated by Expression (22). Note that, in Expression (21) and Expression (22), (x,y) representing the pixel position is omitted.

$$ts0=CH/\mu HS(ts0,0) \quad (21)$$

$$tb0=CH/\mu Hb(tb0,0) \quad (22)$$

Figure 24:
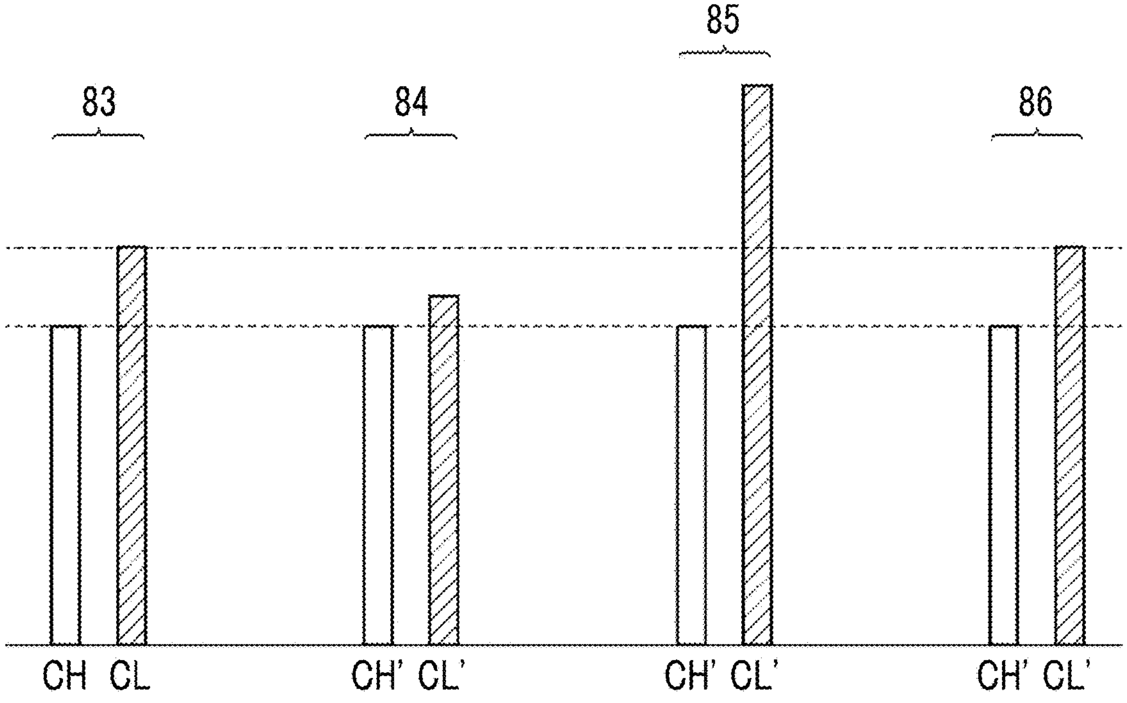
FIG. 24 is a diagram showing an attenuation amount according to a thickness of a bone part and a thickness of a soft part in a high-energy image and a low-energy image.

FIG. 24 is a diagram showing a relationship between the attenuation amounts in accordance with the thickness of the bone part and the thickness of the soft part. In FIG. 24, an attenuation amount 83 indicates the attenuation amount which is the pixel value of the low-energy image and the attenuation amount which is the pixel value of the high-energy image which are derived by actually imaging the subject. For description, in the attenuation amount 83, the attenuation amount which is the pixel value of the low-energy image and the attenuation amount which is the pixel value of the high-energy image are assigned the same reference numerals CL and CH as the first attenuation image and the second attenuation image, respectively. Here, the attenuation amount of the low-energy image and the attenuation amount of the high-energy image are larger as the density of the composition is higher. Therefore, the composition in a case of tb=0 and ts=ts0 has a lower density than the composition based on the actual thickness of the bone part and the actual thickness of the soft part. Therefore, in a case in which tb=0 and ts=ts0, the pixel value, that is, the attenuation amount of the first attenuation image (here, a provisional first attenuation image CL') derived by Expression (16) is smaller than the pixel value of the first attenuation image CL derived from the actual thickness of the bone part and the actual thickness of the soft part (that is, CL>CL') as shown in an attenuation amount 84 of FIG. 24.

On the other hand, the composition in a case in which tb=tb0 and ts=0 has a higher density than the composition based on the actual thickness of the bone part and the actual thickness of the soft part. Therefore, in a case in which tb=tb0 and ts=0, the pixel value, that is, the attenuation amount of the provisional first attenuation image CL' derived by Expression (16) is smaller than the pixel value of the first attenuation image CL derived from the actual thickness of the bone part and the actual thickness of the soft part (that is, CL<CL') as shown in an attenuation amount 85 of FIG. 24.

It should be noted that the pixel value, that is, the attenuation amount of the provisional first attenuation image CL' derived by Expression (16) by using the actual thickness of the bone part and the actual thickness of the soft part is the same as the pixel value of the first attenuation image CL as shown in an attenuation amount 86 of FIG. 24. By using this fact, the image derivation unit 23 derives the thickness tb of the bone part and the thickness ts of the soft part in the following manner.

(Step 1)

First, in Expression (17), a provisional thickness tsk of the soft part is calculated by using the pixel value of the second attenuation image CH and the soft part attenuation coefficient μHs derived for each pixel. It should be noted that zero is used as an initial value of a provisional thickness tbk of the bone part.

(Step 2)

Next, a provisional first attenuation image CL' is calculated by Expression (16) by using the calculated provisional thickness tsk of the soft part, the provisional thickness tbk of the bone part, and the soft part attenuation coefficient μLs and the bone part attenuation coefficient μLb for the low-energy radiation.

(Step 3)

Next, the difference value ΔCL between the provisional first attenuation image CL' and the first attenuation image CL is calculated. The provisional thickness tbk of the bone part is updated on the assumption that the difference value ΔCL is the pixel value corresponding to the amount of the radiation attenuated by the bone.

(Step 4)

Next, a provisional second attenuation image CH' is calculated by Expression (17) by using the updated provisional thickness tsk of the bone part and the provisional thickness tbk of the soft part.

(Step 5)

Next, the difference value ΔCH between the provisional second attenuation image CH' and the second attenuation image CH is calculated. The provisional thickness tsk of the soft part is updated on the assumption that the difference value ΔCH is the pixel value corresponding to the amount of the radiation attenuated by the soft part.

Then, the thickness ts of the soft part and the thickness tb of the bone part are derived by repeating the processing of steps 1 to 5 until the absolute values of the difference values ΔCL and ΔCH are less than a predetermined threshold value. It should be noted that the thickness ts of the soft part and the thickness tb of the bone part may be derived by repeating the processing of steps 1 to 5 a predetermined number of times.

Then, the image derivation unit 23 derives the soft part image Gs based on the derived thickness ts of the soft part, and derives the bone part image Gb based on the derived thickness tb of the bone part. Here, the soft part image Gs has the pixel value of the size corresponding to the thickness ts of the soft part, and the bone part image Gb has the pixel value of the size corresponding to the thickness tb of the bone part.

Figure 25:
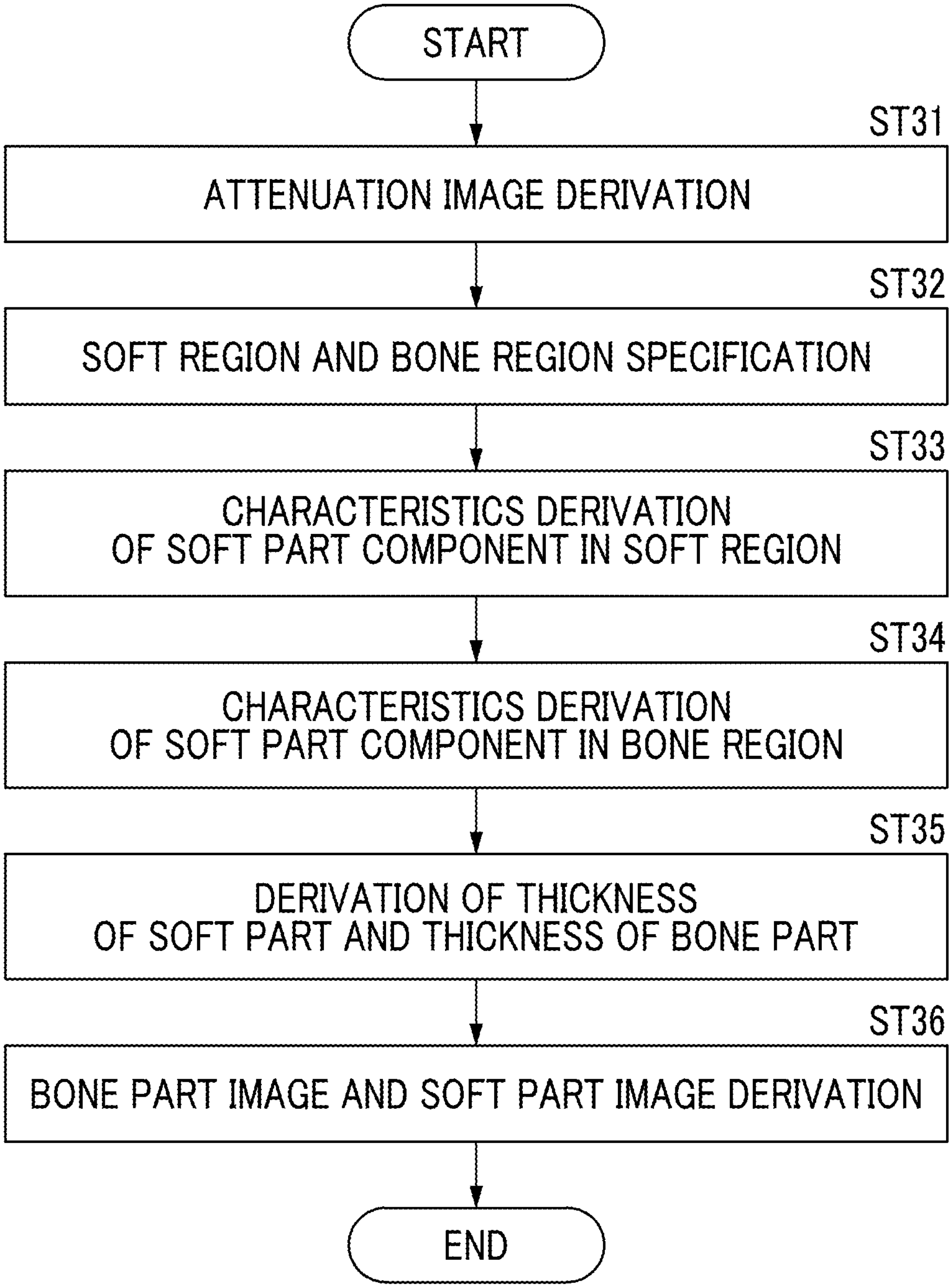
FIG. 25 is a flowchart showing processing performed in a third embodiment of structure image derivation.

Next, processing performed in the third embodiment of the structure image derivation will be described. FIG. 25 is a flowchart showing processing performed in the third embodiment of the structure image derivation. It is assumed that the first and second radiation images are acquired by the information acquisition unit 21 and the scattered ray component is removed by the scattered ray removal unit 22. Next, the image derivation unit 23 derives the first attenuation image CL and the second attenuation image CH from the first radiation image G1 and the second radiation image G2 (attenuation image derivation: step ST31), and specifies the soft region including only the soft part component and the bone region including the bone part in the first attenuation image CL or the second attenuation image CH (step ST32). Next, the image derivation unit 23 derives the characteristic (soft part attenuation coefficient) of the soft part component related to the attenuation of the radiation image in the soft region (step ST33). Subsequently, the image derivation unit 23 derives the characteristics of the soft part component in the bone region (Step ST34).

Next, the image derivation unit 23 derives the thickness ts of the soft part and the thickness tb of the bone part (step ST35), derives the bone part image Gb and the soft part image Gs from the thickness ts of the soft part and the thickness tb of the bone part (step ST36), and ends the processing.

As described above, in the third embodiment of the structure image derivation, the soft part attenuation coefficient is derived based on the characteristic of the soft part component derived in the soft region around the bone region, that is the soft part attenuation coefficient in the bone region including the bone part component in the first radiation image G1 or the second radiation image G2. Then, the soft part image Gs in which the soft part component is emphasized and the bone part image Gb in which the bone part component is emphasized are derived based on the soft part attenuation coefficient in at least the region of the subject H in the first radiation image G1 or the second radiation image G2. Therefore, the soft part attenuation coefficient in the bone region can be derived accurately, and as a result, the soft part image Gs and the bone part image Gb in which the soft part component and the bone part component are separated accurately can be derived.

Figure 26:
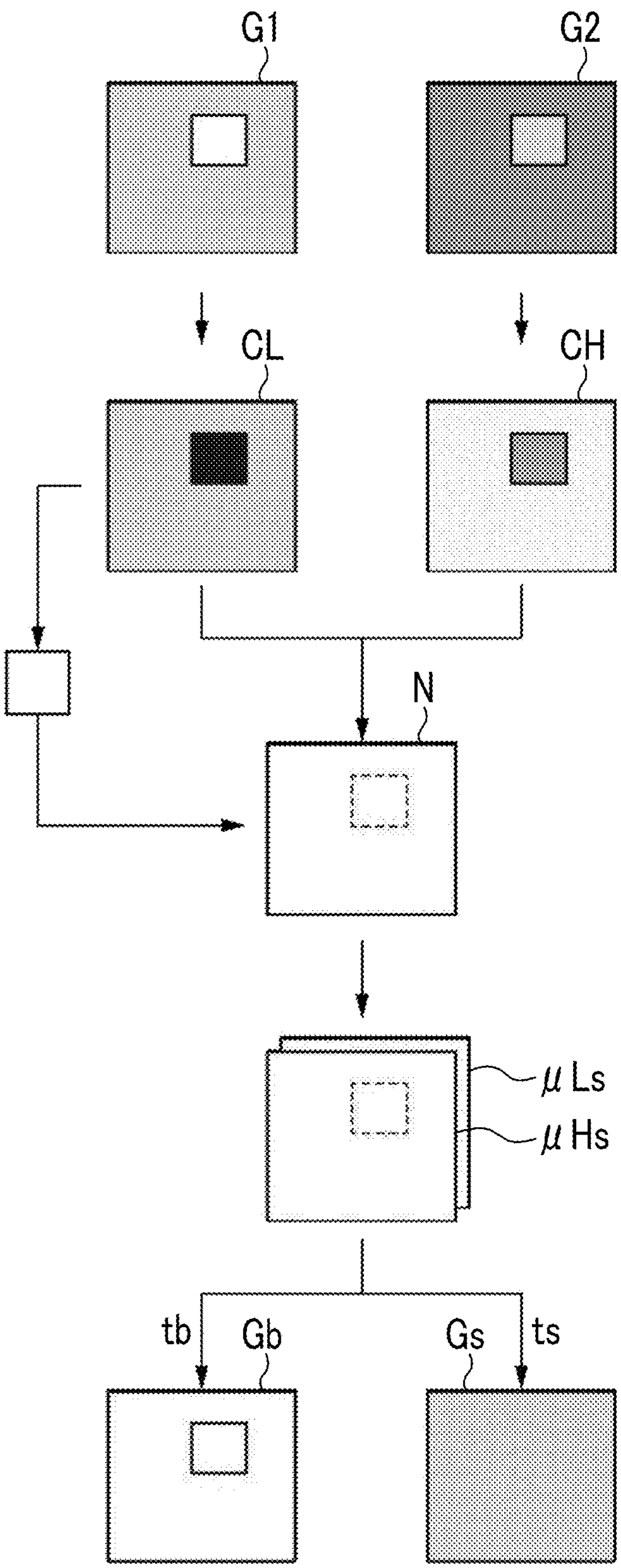
FIG. 26 is a diagram schematically showing processing performed by the radiation image processing device according to the fourth embodiment of the structure image derivation.

Next, a fourth embodiment of the structure image derivation will be described. FIG. 26 is a diagram schematically showing processing performed in the fourth embodiment of the structure image derivation. As shown in FIG. 26, the image derivation unit 23 detects the bone region from the first attenuation image CL or the second attenuation image CH. Note that the bone region may be detected from the first radiation image G1 or the second radiation image G2. For this reason, in the fourth embodiment, the image derivation unit 23 uses a trained model constructed by subjecting a neural network to machine learning so as to detect the bone region from the radiation image or the attenuation image, as in the second embodiment. In this case, the trained model is constructed to detect the bone region by learning the bone region based on the pixel value of the radiation image or the attenuation image.

On the other hand, in the radiation image or the attenuation image, the pixel value of the bone region and the pixel value of the soft region including only the soft part component are significantly different from each other. Therefore, the bone region may be detected from the radiation image or the attenuation image by performing the threshold value processing on the radiation image or the attenuation image. In addition, in the radiation image or the attenuation image, the shape of the bone region is specified by the difference between the pixel value of the bone region and the pixel value of the soft region including only the soft part component. Therefore, the bone region may be detected from the radiation image or the attenuation image by the template matching using the shape of the bone region according to a part of the subject H included in the radiation image or the attenuation image.

In the fourth embodiment of the structure image derivation, the image derivation unit 23 derives the soft part attenuation coefficient in the bone region specified based on the pixel value of the radiation image or the attenuation image as described above. Since the processing after the derivation of the soft part attenuation coefficient in the bone region is the same as the processing in the third embodiment of the structure image derivation, the detailed description thereof will be omitted here.

In the third and fourth embodiments of the structure image derivation, the soft part attenuation coefficient is derived using the first attenuation image CL and the second attenuation image CH, and the bone part image Gb and the soft part image Gs are derived. However, the present disclosure is not limited thereto. The soft part attenuation coefficient may be derived from the first radiation image G1 and the second radiation image G2, and the thickness of the bone part and the thickness of the soft part may be derived to derive the bone part image Gb and the soft part image Gs.

Further, the radiation in the embodiments described above is not particularly limited, and α-rays or γ-rays can be used in addition to X-rays.

In addition, in the above-described embodiment, for example, as a hardware structure of processing units that execute various types of processing, such as the information acquisition unit 21, the scattered ray removal unit 22, the image derivation unit 23, the information derivation unit 24, the learning unit 25, the training data derivation unit 26, and the display control unit 27, various processors shown below can be used. The various processors include a programmable logic device (PLD) which is a processor whose circuit configuration is changeable after manufacturing such as a field programmable gate array (FPGA), a dedicated electric circuit which is a processor having a circuit configuration exclusively designed to execute specific processing such as an application specific integrated circuit (ASIC), and the like, in addition to the CPU which is a general-purpose processor that executes software (program) to function as various processing units, as described above.

One processing unit may be configured by one of the various processors or a combination of two or more processors of the same type or different types (for example, a combination of a plurality of FPGAs or a combination of a CPU and an FPGA). Further, the plurality of processing units may be configured of one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as a hardware structure.

Further, more specifically, a circuitry combining circuit elements such as semiconductor elements can be used as the hardware structure of the various processors.

The supplementary notes of the present disclosure will be described below.

(Supplementary Note 1)

An image processing device comprising:

at least one processor, in which the processor acquires a structure image representing at least one structure in a subject based on at least one radiation image of the subject, and derives a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

(Supplementary Note 2)

The image processing device according to Supplementary Note 1, in which the processor acquires a first radiation image and a second radiation image acquired by imaging a subject including a bone part and a soft part with radiation having different energy distributions, and derives the structure image by performing weighting subtraction on the first radiation image and the second radiation image.

(Supplementary Note 3)

The image processing device according to Supplementary Note 2, in which the processor removes scattered ray components of the first radiation image and the second radiation image to derive a first primary ray image and a second primary ray image, and derives the structure image based on the first primary ray image and the second primary ray image.

(Supplementary Note 4)

The image processing device according to any one of Supplementary Notes 1 to 3, in which the structure is a bone part included in the subject, and the composition information is a bone density.

(Supplementary Note 5)

The image processing device according to Supplementary Note 4, in which the bone part is a femur.

(Supplementary Note 6)

The image processing device according to Supplementary Note 4, in which the bone part is a vertebra.

(Supplementary Note 7)

The image processing device according to any one of Supplementary Notes 1 to 6, in which the structure is a soft part included in the subject, and the composition information is a thickness of the soft part.

(Supplementary Note 8)

A learning device comprising:

at least one processor, in which the processor performs training of a neural network using training data including a training structure image including at least one structure in a subject, a deviation angle of radiation with respect to a reference position for the structure included in the training structure image, and composition information of the structure included in the training structure image at the reference position, and constructs a trained model that outputs an estimation result of the deviation angle of the radiation with respect to the reference position of the structure and the composition information of the structure at the reference position included in the structure image by input of the structure image including at least one structure in the subject, by the training.

(Supplementary Note 9)

The learning device according to supplementary note 8, in which the processor derives the training structure image by projecting the structure included in a three-dimensional image of the subject based on a deviation angle with respect to the reference position, and derives the training data by deriving composition information of the structure as composition information of the structure at the reference position in a case where the structure included in the three-dimensional image is projected in a reference direction in which the structure is the reference position.

(Supplementary Note 10)

The learning device according to supplementary note 9, in which the structure is a bone part, and the processor derives a three-dimensional bone density of the bone part included in the three-dimensional image, and derives a two-dimensional bone density of the bone part as the composition information of the structure at the reference position by multiplying the three-dimensional bone density by a thickness of the bone part in the reference direction.

(Supplementary Note 11)

An image processing method comprising:

acquiring a structure image representing at least one structure in a subject based on at least one radiation image of the subject; and deriving a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

(Supplementary Note 12)

A learning method comprising:

performing training of a neural network using training data including a training structure image including at least one structure in a subject, a deviation angle of radiation with respect to a reference position for the structure included in the training structure image, and composition information of the structure included in the training structure image at the reference position, and constructing a trained model that outputs an estimation result of the deviation angle of the radiation with respect to the reference position of the structure and the composition information of the structure at the reference position included in the structure image by input of the structure image including at least one structure in the subject, by the training.

(Supplementary Note 13)

An image processing program causing a computer to execute a process comprising: acquiring a structure image representing at least one structure in a subject based on at least one radiation image of the subject; and deriving a deviation angle of the structure included in the structure image with respect to a reference position and composition information of the structure at the reference position by using a trained model that outputs an estimation result of a deviation angle of radiation with respect to the reference position for the structure included in the structure image and the composition information of the structure at the reference position by input of the structure image.

(Supplementary Note 14)

A learning program causing a computer to execute a process comprising:

performing training of a neural network using training data including a training structure image including at least one structure in a subject, a deviation angle of radiation with respect to a reference position for the structure included in the training structure image, and composition information of the structure included in the training structure image at the reference position, and constructing a trained model that outputs an estimation result of the deviation angle of the radiation with respect to the reference position of the structure and the composition information of the structure at the reference position included in the structure image by input of the structure image including at least one structure in the subject, by the training.

What is claimed is:

1. An image processing device comprising:

at least one processor, wherein the at least one processor is configured to:

acquire a structure image representing at least one structure in a subject based on at least one radiation image of the subject, and derive a deviation angle of the at least one structure included in the structure image with respect to a reference position and composition information of the at least one structure at the reference position by using a trained model that is configured to output an estimation result of the deviation angle of the at least one structure with respect to the reference position for the at least one structure included in the structure image and the composition information of the at least one structure at the reference position by input of the structure image.

2. The image processing device according to claim 1, wherein the at least one radiation image comprises a first radiation image and a second radiation image and the at least one processor is configured to acquire the first radiation image and the second radiation image acquired by imaging the subject, the subject including a bone part and a soft part with radiation having different energy distributions, and derives the structure image by performing weighting subtraction on the first radiation image and the second radiation image.

3. The image processing device according to claim 2, wherein the at least one processor removes scattered ray components of the first radiation image and the second radiation image to derive a first primary ray image and a second primary ray image, and derives the structure image based on the first primary ray image and the second primary ray image.

4. The image processing device according to claim 1, wherein the at least one structure is a bone part included in the subject, and the composition information is a bone density.

5. The image processing device according to claim 4, wherein the bone part is a femur.

6. The image processing device according to claim 4, wherein the bone part is a vertebra.

7. The image processing device according to claim 1, wherein the at least one structure is a soft part included in the subject, and the composition information is a thickness of the soft part.

8. A learning device comprising:

at least one processor, wherein the at least one processor is configured to:

perform training of a neural network using training data including a training structure image including at least one structure in a subject, a deviation angle of radiation with respect to a reference position for the at least one structure included in the training structure image, and composition information of the at least one structure included in the training structure image at the reference position, and construct a trained model that is configured to output an estimation result of the deviation angle of the radiation with respect to the reference position of the at least one structure and the composition information of the at least one structure at the reference position included in the training structure image by input of the training structure image including the at least one structure in the subject, by the training.

9. The learning device according to claim 8, wherein the at least one processor derives the training structure image by projecting the at least one structure included in a three-dimensional image of the subject based on the deviation angle with respect to the reference position, and derives the training data by deriving composition information of the at least one structure as composition information of the at least one structure at the reference position in a case where the at least one structure included in the three-dimensional image is projected in a reference direction in which the at least one structure is at the reference position.

10. The learning device according to claim 9, wherein the at least one structure is a bone part, and the at least one processor derives a three-dimensional bone density of the bone part included in the three-dimensional image, and derives a two-dimensional bone density of the bone part as the composition information of the at least one structure at the reference position by multiplying the three-dimensional bone density by a thickness of the bone part in the reference direction.

11. An image processing method comprising:

acquiring a structure image representing at least one structure in a subject based on at least one radiation image of the subject; and deriving a deviation angle of the at least one structure included in the structure image with respect to a reference position and composition information of the at least one structure at the reference position by using a trained model that outputs an estimation result of the deviation angle of the at least one structure with respect to the reference position for the at least one structure included in the structure image and the composition information of the at least one structure at the reference position by input of the structure image.

12. A learning method comprising:

performing training of a neural network using training data including a training structure image including at least one structure in a subject, a deviation angle of radiation with respect to a reference position for the at least one structure included in the training structure image, and composition information of the at least one structure included in the training structure image at the reference position, and constructing a trained model that outputs an estimation result of the deviation angle of the radiation with respect to the reference position of the at least one structure and the composition information of the at least one structure at the reference position included in the training structure image by input of the training structure image including the at least one structure in the subject, by the training.

13. A non-transitory computer-readable storage medium that stores an image processing program causing a computer to execute a process comprising:

acquiring a structure image representing at least one structure in a subject based on at least one radiation image of the subject; and deriving a deviation angle of the at least one structure included in the structure image with respect to a reference position and composition information of the at least one structure at the reference position by using a trained model that outputs an estimation result of the deviation angle of the at least one structure with respect to the reference position for the at least one structure included in the structure image and the composition information of the at least one structure at the reference position by input of the structure image.

14. A non-transitory computer-readable storage medium that stores a learning program causing a computer to execute a process comprising:

performing training of a neural network using training data including a training structure image including at least one structure in a subject, a deviation angle of radiation with respect to a reference position for the at least one structure included in the training structure image, and composition information of the at least one structure included in the training structure image at the reference position, and constructing a trained model that outputs an estimation result of the deviation angle of the radiation with respect to the reference position of the at least one structure and the composition information of the at least one structure at the reference position included in the training structure image by input of the training structure image including the at least one structure in the subject, by the training.

* * * * *